US008992493B2

(12) United States Patent
Croteau et al.

(10) Patent No.: US 8,992,493 B2
(45) Date of Patent: Mar. 31, 2015

(54) CHEST DRAINAGE SYSTEMS AND METHODS

(75) Inventors: James Croteau, Fitchburg, MA (US); Theodore Karwoski, Hollis, NH (US); Joanne Krawczyk, Dunstable, MA (US); Marc Larochelle, Bedford, NH (US); Patrick Lee, Long Grove, IL (US); Nicholas Want, Manchester, NH (US)

(73) Assignee: Atrium Medical Corporation, Merrimack, NH (US)

( * ) Notice: Subject to any disclaimer, the term of this patent is extended or adjusted under 35 U.S.C. 154(b) by 12 days.

(21) Appl. No.: 13/634,116

(22) PCT Filed: Jan. 28, 2011

(86) PCT No.: PCT/US2011/022985
§ 371 (c)(1),
(2), (4) Date: Nov. 9, 2012

(87) PCT Pub. No.: WO2011/112291
PCT Pub. Date: Sep. 15, 2011

(65) Prior Publication Data
US 2013/0110057 A1   May 2, 2013

Related U.S. Application Data

(63) Continuation-in-part of application No. 12/723,074, filed on Mar. 12, 2010, now Pat. No. 8,882,678.

(60) Provisional application No. 61/160,037, filed on Mar. 13, 2009.

(51) Int. Cl.
*A61M 1/00* (2006.01)
*A61B 5/08* (2006.01)
(Continued)

(52) U.S. Cl.
CPC ........... *A61M 1/0031* (2013.01); *A61M 1/0019* (2013.01); *A61M 1/0037* (2013.01);
(Continued)

(58) Field of Classification Search
CPC ............ A61M 1/0001; A61M 1/0023; A61M 1/0031; A61M 1/0037; A61M 1/0049; A61M 27/00; A61M 2001/0001; A61M 2001/0023; A61M 2001/0025; A61M 2001/0027; A61M 2001/0031; A61M 2001/0035; A61M 2205/15; A61M 2205/12; A61M 2205/121; A61M 2205/123; A61M 2205/3355; A61M 2205/583; A61M 2205/584; A61M 1/0019; A61M 1/008; A61M 1/0035; A61M 2205/05
USPC ......... 604/540, 541, 543, 319, 320, 119, 120, 604/246, 247, 30, 31, 315, 317, 65, 66, 67
See application file for complete search history.

(56) References Cited

U.S. PATENT DOCUMENTS 3,693,613 A   9/1972   Kelman
3,902,495 A   9/1975   Weiss et al.
(Continued)

FOREIGN PATENT DOCUMENTS

EP   2080530 A1   7/2009
WO   WO 0026537 A1   5/2000
(Continued)

OTHER PUBLICATIONS

International Search Report dated Jul. 20, 2011, application No. PCT/US1122985.
(Continued)

*Primary Examiner* — Adam Marcetich

(57) ABSTRACT

A chest drainage system includes a collection device and a fluid pathway configured to extend from the collection device to a patient. The fluid pathway has a proximal portion configured to extend proximally toward the patient and a distal portion configured to extend distally from the patient. The chest drainage system also includes a pressure source including an accumulator configured to selectively provide sub-atmospheric pressure to the distal portion of the fluid pathway and a valve configured to selectively relieve pressure in the proximal portion of the fluid pathway. The system is configured to open the valve and to introduce the sub-atmospheric pressure from the accumulator of the pressure source when a predetermined pressure differential is detected between the proximal and distal portions of the fluid pathway.

13 Claims, 19 Drawing Sheets

(51) Int. Cl.
*A61M 27/00* (2006.01)
*A61B 19/00* (2006.01)

(52) U.S. Cl.
CPC ............... *A61M 1/008* (2013.01); *A61B 5/08* (2013.01); *A61B 19/54* (2013.01); *A61M 27/00* (2013.01); *A61M 2210/101* (2013.01)
USPC ........... 604/318; 604/319; 604/323; 604/540; 604/541; 604/543

(56) References Cited

U.S. PATENT DOCUMENTS

| | | | |
|---|---|---|---|
| 3,938,540 A * | 2/1976 | Holbrook et al. ............. 137/205 |
| 3,946,735 A | 3/1976 | DeWall | |
| 3,982,546 A | 9/1976 | Friend | |
| 4,015,603 A | 4/1977 | Kurtz et al. | |
| 4,018,224 A | 4/1977 | Kurtz et al. | |
| 4,052,987 A * | 10/1977 | Wuchinich et al. ............. 604/65 |
| 4,073,294 A | 2/1978 | Stanley et al. | |
| 4,112,948 A | 9/1978 | Kurtz et al. | |
| 4,233,983 A | 11/1980 | Rocco | |
| 4,287,889 A | 9/1981 | Stupar | |
| 4,296,748 A | 10/1981 | Kurtz et al. | |
| 4,324,262 A | 4/1982 | Hall | |
| 4,327,720 A | 5/1982 | Bronson | |
| 4,372,336 A | 2/1983 | Cornell et al. | |
| 4,396,386 A | 8/1983 | Kurtz et al. | |
| 4,405,309 A | 9/1983 | Kurtz et al. | |
| 4,425,125 A | 1/1984 | Kurtz et al. | |
| 4,439,189 A | 3/1984 | Sargeant et al. | |
| 4,439,190 A | 3/1984 | Protzmann et al. | |
| 4,455,141 A | 6/1984 | Todd | |
| 4,468,226 A | 8/1984 | Kurtz et al. | |
| 4,469,484 A | 9/1984 | Kurtz et al. | |
| 4,475,904 A * | 10/1984 | Wang ............................ 604/119 |
| 4,493,698 A * | 1/1985 | Wang et al. .................... 604/541 |
| 4,519,796 A | 5/1985 | Russo | |
| 4,542,643 A | 9/1985 | Himmelstein | |
| 4,563,171 A | 1/1986 | Bodicky | |
| 4,569,674 A | 2/1986 | Phillips et al. | |
| 4,578,060 A | 3/1986 | Huck et al. | |
| 4,619,647 A | 10/1986 | Kurtz et al. | |
| 4,643,197 A | 2/1987 | Greene et al. | |
| 4,650,476 A | 3/1987 | Telang | |
| 4,650,477 A | 3/1987 | Johnson | |
| 4,654,029 A | 3/1987 | D'Antonio | |
| 4,655,745 A | 4/1987 | Corbett | |
| 4,675,010 A | 6/1987 | Siposs et al. | |
| 4,675,011 A | 6/1987 | Kurtz et al. | |
| 4,715,855 A | 12/1987 | D'Antonio et al. | |
| 4,735,606 A | 4/1988 | Davison | |
| 4,740,202 A | 4/1988 | Stacey et al. | |
| 4,747,843 A | 5/1988 | Felix et al. | |
| 4,747,844 A | 5/1988 | Elliott | |
| 4,767,417 A | 8/1988 | Boehringer et al. | |
| 4,781,678 A | 11/1988 | de Couet et al. | |
| 4,784,642 A | 11/1988 | Everett, Jr. et al. | |
| 4,822,346 A | 4/1989 | Elliott | |
| 4,826,494 A | 5/1989 | Richmond et al. | |
| 4,828,552 A | 5/1989 | Malette | |
| 4,832,685 A | 5/1989 | Haines | |
| 4,883,476 A | 11/1989 | Kurtz et al. | |
| 4,889,531 A | 12/1989 | D'Antonio et al. | |
| 4,894,056 A | 1/1990 | Bommarito | |
| 4,902,284 A | 2/1990 | D'Antonio et al. | |
| 4,911,697 A | 3/1990 | Kerwin | |
| 4,923,451 A | 5/1990 | McCormick | |
| 4,929,244 A | 5/1990 | Swisher | |
| 4,955,874 A | 9/1990 | Farrar et al. | |
| 4,963,135 A | 10/1990 | Kerwin | |
| 4,990,137 A | 2/1991 | Graham | |
| 4,994,050 A | 2/1991 | Weilbacher et al. | |
| 5,019,060 A | 5/1991 | Goosen | |
| 5,026,358 A | 6/1991 | Everett, Jr. et al. | |
| 5,037,407 A | 8/1991 | Kurtz | |
| 5,141,503 A | 8/1992 | Sewell, Jr. | |
| 5,158,533 A | 10/1992 | Strauss et al. | |
| 5,286,262 A | 2/1994 | Herweck et al. | |
| 5,300,050 A | 4/1994 | Everett, Jr. et al. | |
| 5,370,610 A | 12/1994 | Reynolds | |
| 5,380,314 A | 1/1995 | Herweck et al. | |
| 5,397,299 A | 3/1995 | Karwoski et al. | |
| 5,507,734 A | 4/1996 | Everett, Jr. et al. | |
| 5,520,652 A | 5/1996 | Peterson | |
| 5,643,229 A | 7/1997 | Sinaiko | |
| 5,738,656 A * | 4/1998 | Wagner ......................... 604/119 |
| 5,800,393 A | 9/1998 | Sahota | |
| 5,807,358 A | 9/1998 | Herweck et al. | |
| 5,897,534 A | 4/1999 | Heim et al. | |
| 5,931,821 A | 8/1999 | Weilbacher et al. | |
| 5,944,703 A | 8/1999 | Dixon et al. | |
| 5,971,956 A | 10/1999 | Epstein | |
| 5,989,234 A | 11/1999 | Valerio et al. | |
| 6,007,521 A | 12/1999 | Bidwell | |
| 6,017,493 A | 1/2000 | Cambron et al. | |
| 6,024,731 A | 2/2000 | Seddon et al. | |
| 6,099,493 A | 8/2000 | Swisher | |
| 6,123,697 A | 9/2000 | Shippert | |
| 6,142,982 A * | 11/2000 | Hunt et al. .................... 604/313 |
| 6,254,591 B1 | 7/2001 | Roberson | |
| 6,283,719 B1 | 9/2001 | Frantz et al. | |
| 6,299,593 B1 | 10/2001 | Wakabayashi | |
| 6,338,728 B1 | 1/2002 | Valerio et al. | |
| 6,352,525 B1 | 3/2002 | Wakabayashi | |
| 6,371,124 B1 | 4/2002 | Whelan | |
| 6,371,947 B1 | 4/2002 | Gibertoni | |
| 6,428,508 B1 * | 8/2002 | Ross .............................. 604/118 |
| 6,447,491 B1 | 9/2002 | Lord | |
| 6,514,232 B1 | 2/2003 | Gibertoni | |
| 6,537,495 B1 | 3/2003 | Cambron et al. | |
| 6,558,341 B1 | 5/2003 | Swisher | |
| 6,592,602 B1 | 7/2003 | Peartree et al. | |
| 6,626,877 B2 | 9/2003 | Anderson et al. | |
| 6,749,592 B2 | 6/2004 | Lord | |
| 6,837,868 B1 | 1/2005 | Fajnsztajn | |
| 6,849,061 B2 | 2/2005 | Wagner | |
| 6,881,204 B1 | 4/2005 | Bunce | |
| 6,902,550 B2 | 6/2005 | Want et al. | |
| 6,955,664 B2 | 10/2005 | D'Antonio | |
| 6,976,977 B2 | 12/2005 | Yam | |
| 7,207,946 B2 | 4/2007 | Sirokman | |
| 7,264,616 B2 | 9/2007 | Shehada et al. | |
| 7,326,197 B2 | 2/2008 | Breznock | |
| 7,419,483 B2 | 9/2008 | Shehada | |
| 7,674,248 B2 | 3/2010 | Anderson et al. | |
| 7,695,467 B2 | 4/2010 | Breznock | |
| 8,070,736 B2 | 12/2011 | Nishtala | |
| 8,075,539 B2 | 12/2011 | Nishtala | |
| 8,152,786 B2 | 4/2012 | Shapland | |
| 8,252,003 B2 | 8/2012 | Tanaka | |
| 8,267,917 B2 | 9/2012 | Jabbour | |
| 2001/0056273 A1 | 12/2001 | Ewers | |
| 2002/0058915 A1 | 5/2002 | Wakabayashi | |
| 2002/0082568 A1 | 6/2002 | Yam | |
| 2002/0193761 A1 | 12/2002 | Lord | |
| 2002/0198505 A1 | 12/2002 | Want et al. | |
| 2003/0028175 A1 | 2/2003 | D'Antonio | |
| 2003/0100890 A1 | 5/2003 | Waddell | |
| 2004/0040560 A1 | 3/2004 | Euliano | |
| 2004/0059303 A1 | 3/2004 | Anderson et al. | |
| 2004/0078026 A1 | 4/2004 | Wagner | |
| 2004/0106874 A1 | 6/2004 | Eigler | |
| 2004/0143227 A1 | 7/2004 | Rollin et al. | |
| 2004/0143228 A1 | 7/2004 | Anderson et al. | |
| 2004/0204693 A1 | 10/2004 | Anderson et al. | |
| 2004/0230179 A1 | 11/2004 | Shehada | |
| 2004/0260255 A1 | 12/2004 | Charlez | |
| 2004/0267215 A1 | 12/2004 | Charlez et al. | |
| 2005/0016287 A1 | 1/2005 | Corbeil et al. | |
| 2005/0054994 A1 | 3/2005 | Cioanta | |
| 2005/0137539 A1 | 6/2005 | Biggie et al. | |
| 2005/0154359 A1 | 7/2005 | Charlez | |
| 2005/0154373 A1 | 7/2005 | Deutsch | |
| 2005/0192548 A1 | 9/2005 | Dolliver et al. | |

(56) References Cited

U.S. PATENT DOCUMENTS

| | | | |
|---|---|---|---|
| 2006/0036221 A1 | 2/2006 | Watson, Jr. | |
| 2006/0122575 A1 | 6/2006 | Wakabayashi | |
| 2006/0149170 A1* | 7/2006 | Boynton et al. | 601/6 |
| 2006/0149599 A1 | 7/2006 | Fox | |
| 2006/0206097 A1 | 9/2006 | Breznock | |
| 2007/0010798 A1 | 1/2007 | Stoller et al. | |
| 2007/0038170 A1 | 2/2007 | Joseph | |
| 2007/0056264 A1 | 3/2007 | Hou | |
| 2007/0078444 A1* | 4/2007 | Larsson | 604/540 |
| 2007/0100324 A1 | 5/2007 | Tempel | |
| 2007/0142742 A1 | 6/2007 | Aljuri | |
| 2007/0219488 A1 | 9/2007 | Francescatti | |
| 2007/0219532 A1 | 9/2007 | Karpowicz et al. | |
| 2007/0219534 A1 | 9/2007 | Phung et al. | |
| 2007/0219537 A1 | 9/2007 | Phung | |
| 2008/0033028 A1 | 2/2008 | Berthelette | |
| 2008/0103523 A1 | 5/2008 | Chiu | |
| 2008/0114300 A1* | 5/2008 | Muri et al. | 604/131 |
| 2008/0119802 A1 | 5/2008 | Riesinger | |
| 2008/0183156 A1 | 7/2008 | Yoo | |
| 2008/0269582 A1 | 10/2008 | Mansour et al. | |
| 2009/0030383 A1* | 1/2009 | Larsen et al. | 604/290 |
| 2009/0157019 A1 | 6/2009 | Koch et al. | |
| 2009/0163853 A1* | 6/2009 | Cull et al. | 604/35 |
| 2009/0163863 A1* | 6/2009 | Lutwyche | 604/119 |
| 2009/0188531 A1 | 7/2009 | Boyle, Jr. | |
| 2009/0198201 A1* | 8/2009 | Adahan | 604/319 |
| 2009/0235935 A1 | 9/2009 | Pacey | |
| 2009/0264833 A1 | 10/2009 | Boyle, Jr. | |
| 2009/0264837 A1 | 10/2009 | Adahan | |
| 2009/0266146 A1 | 10/2009 | Fontanili et al. | |
| 2009/0281523 A1 | 11/2009 | Sacco | |
| 2010/0222754 A1 | 9/2010 | Nishtala | |
| 2011/0060300 A1* | 3/2011 | Weig et al. | 604/319 |
| 2011/0190737 A1 | 8/2011 | Rocco | |

FOREIGN PATENT DOCUMENTS

| | | |
|---|---|---|
| WO | WO 2004110523 A1 | 12/2004 |
| WO | WO 2007024230 A1 | 3/2007 |
| WO | WO 2009005424 A1 | 1/2009 |
| WO | WO 2009120400 A3 | 2/2010 |
| WO | WO 2010021775 A1 | 2/2010 |
| WO | WO 2010026458 A1 | 3/2010 |

OTHER PUBLICATIONS

U.S. Appl. No. 29/357,469, filed Dec. 30, 2004, Want et al.

* cited by examiner

CHEST DRAINAGE SYSTEMS AND METHODS

CROSS REFERENCE TO RELATED APPLICATIONS

This application is the U.S. National Phase application of PCT International Application No. PCT/US2011/022985, filed Jan. 28, 2011 which is a continuation-in-part of U.S. patent application Ser. No. 12/723,074, filed Mar. 12, 2010, entitled "PLEURAL DRAINAGE SYSTEM AND METHOD OF USE," which claims the benefit of U.S. Provisional Patent Application No. 61/160,037, filed Mar. 13, 2009, the contents of which applications are incorporated herein by reference in their entirety.

FIELD OF THE INVENTION

The field of the invention relates generally to medical drainage systems, and more particularly to chest drainage systems.

BACKGROUND OF THE INVENTION

A number of fluid recovery systems have been developed for draining fluid, such as air and/or blood, from a patient. An example of such a fluid recovery system is a chest drainage system. Chest drainage systems are intended to remove fluid from the pleural space or the mediastinal cavity and to restore the sub-atmospheric pressure that is normally present in the pleural space. The systems are usually adapted to allow suction to be applied to the chest cavity to facilitate, among other things, the removal of fluid from the pleural space. Once the fluid has been removed, the pleural cavity is allowed to heal and the normal subatmospheric condition of the pleural space is restored.

Over the years, various drainage systems have been proposed. For example, U.S. Pat. No. 4,605,400 discloses a surgical draining apparatus having an air leak indicating means for indicating the directional flow of any gases through a passageway and optionally the qualitative quantity of these gases. The air leak indicating means includes a liquid trap which is visible through the container. Thus as any gases flow therethrough, bubbles are formed which serve as visible indicators of such a flow and of a patient air leak. No bubbling through the liquid indicates a proper operation of the drainage apparatus. However, continuous bubbling through the liquid indicates either an air leak in the connections or an air leak in the pleural cavity of the patient. The gases pass through an aperture which is uppermost in a slanted divider member. However, as the flow of gases increases, the gases additionally flow through succeeding lower apertures along the length of the divider member. Thus, the lowermost of the apertures through which the gases bubble indicates the volume of flow through the air leak indicating means. Suitable indicia are provided on the outside of the drainage apparatus to indicate this to the user.

U.S. Pat. No. 4,654,029 discloses an electronic drainage system including a combination of electronic and mechanical components for measuring and displaying values for air flow, suction, patient negativity and maximum negativity. A patient air flow transducer is located to measure the flow rate of air and other gases in a conduit from the patient. A signal processor is electrically connected to the transducer to convert the signal from the transducer to a form needed by an air flow display. The readout of the display can be provided in units of liters per minute. A patient negativity transducer is also provided in the air conduit to measure the negative pressure in the pleural space. Since larger levels of negativity may occur while an attendant monitoring the system is away from the patient, it may be useful for the physician to know what maximum level of negative pressure was actually attained (e.g., if the tube inserted into the pleural space becomes clogged with blood clots, damaged tissue or the like). In order to clear a blockage, the attendant "milks" the tube in an attempt to reopen it, however, this procedure often causes high values of momentary negativity on the patient. In order to determine that this has happened and to what extent, a maximum negativity hold device is electrically connected to the signal processor and is so devised as to record and store negativity values up to the level permitted by an excessive negativity release or safety valve. The stored value is displayed on a display function. Also, a weight transducer is electronically connected with a fluid collection chamber for weighing the fluid in the chamber as a function of time. The weight transducer and an associated processor and display, enable the measurement and recording of the parameter fluid versus time.

U.S. Pat. No. 4,740,202 relates to a portable suction system in which the vacuum for suction purposes is provided by evacuating a rigid plastic chamber connected to a vacuum pump. A disposable bag is affixed to a suction port on the chamber's cap. In operation, the rigid chamber is evacuated by the vacuum pump, thus drawing air and fluids through a suction tip into a suction port and into the flexible collection bag where the liquids are retained for collection.

In U.S. Pat. No. 6,352,525, an entire drainage system is made completely portable by combining a vacuum pump, a power source, a vacuum chamber, and a collection unit into a single unit. A vacuum chamber, vacuum pump housing, and collection reservoir are removably connected to the chest tube drainage system, each component of the drainage system being generally disposable. A flow meter is interposed between the vacuum chamber and the vacuum pump housing to indicate the amount of air flow. The flow meter includes a flow meter tube within which a floating ball rests. The diameter of the floating ball, the weight of the floating ball, and the inner diameter of the flow meter tube are configured such that the floating ball rests substantially near the bottom of the flow meter tube when there is little or no leak from a patient's lung(s), and such that the floating ball rests substantially near the top of the flow meter tube when a substantial leak exists in a patient's lung(s). In the context of a patient recovering from lung-related surgery, the flow meter indicates an amount of air leak from the patient's lung(s). The amount of air flow through a chest tube is indicated by the flow meter, and a practitioner may adjust a potentiometer until flow characteristics indicated by the flow meter correspond favorably to an amount of air leak which may persist for some time at a lung.

U.S. Pat. No. 7,207,946 discloses a method of providing a signal indicating information related to air evacuation from a chest cavity. An air escapement conduit is inserted into an air evacuation pathway between the chest cavity and a vacuum source, allowing an air flow in response to a pressure differential, generating a signal related to the air flow, and indicating air evacuation information in response to the signal. The air escapement conduit includes a bubble chamber having a fluid disposed between an inlet port and an outlet port so that air flowing between the ports flows through the fluid and forms bubbles. Bubbles in the fluid are counted and a bubble detection signal related to counted bubbles is generated. A difference in air pressure between the ports is detected, and a signal related to the difference is generated. A flash of light provided by a light emitting diode indicates when the air evacuated per selected unit of time exceeds a predetermined level. Data representative of the signal may be stored.

Despite many developments in the field of fluid drainage, however, there remains a need for improved drainage systems, particularly improved chest drainage systems.

SUMMARY OF THE INVENTION

In one aspect of this invention, a chest drainage system is provided. It includes a collection device and a fluid pathway configured to extend from the collection device to a patient. The fluid pathway has a proximal portion configured to extend proximally toward the patient and a distal portion configured to extend distally from the patient. The chest drainage system also includes a pressure source configured to selectively provide sub-atmospheric pressure to the distal portion of the fluid pathway and a valve configured to selectively relieve pressure in the proximal portion of the fluid pathway. The pressure source includes a pressure accumulator configured to store the sub-atmospheric pressure. The system is configured to open the valve and to introduce the sub-atmospheric pressure from the pressure source when a predetermined pressure differential is detected between the proximal and distal portions of the fluid pathway.

According to another aspect, this invention provides a chest drainage system including a collection device and a fluid pathway configured to extend from the collection device to a patient. The fluid pathway has a proximal portion configured to extend proximally toward the patient and a distal portion configured to extend distally from the patient. The chest drainage system also includes a sensor system configured to sense a pressure differential between the proximal and distal portions of the fluid pathway. A means is provided for substantially clearing a blockage in the fluid pathway between the proximal and distal portions of the fluid pathway, and a means is provided for determining when to actuate the clearing means based on at least one of the pressure differential sensed by the sensor system and an elapsed time of operation of the chest drainage system.

According to yet another aspect, this invention provides a chest drainage system including a collection device configured to receive fluid from the pleural cavity of a patient. It also includes means for detecting a pressure differential in the fluid. A display is configured to display a trend in occurrences of changes in pressure of the fluid over time in predetermined time increments based on a number of detections of pressure differentials that exceed a predetermined pressure differential during each of the predetermined time increments, the trend being correlative to the percentage of time that the patient is deemed to have an air leak in the pleural cavity in the predetermined time increments. The display is derived from a ratio of the quantity of respiratory cycles of the patient for which the predetermined pressure differential is detected ($QRC_{leak}$) in the predetermined time increments to the total quantity of respiratory cycles of the patient in respective predetermined time increments ($QRC_{total}$).

According to still another aspect, this invention provides a chest drainage system including a removable and/or replaceable collection canister having at least one inlet port and at least one outlet port; a fluid pathway configured to extend from the at least one inlet port of the removable and/or replaceable collection canister to a patient; and a reusable body portion having at least one inlet port releasably coupled to the at least one outlet port of the removable and/or replaceable collection canister. The reusable body portion has a sensor for detecting whether the at least one inlet port of the reusable body portion is coupled to the at least one outlet port of the removable and/or replaceable collection canister. The removable and/or replaceable collection canister is configured to collect fluid via the fluid pathway either with or without suction applied when coupled to the reusable body portion, to automatically close the at least one outlet part of the removable and/or replaceable collection canister and collect fluid via the fluid pathway when uncoupled from the reusable body portion, and to be alternated between gravity- and suction-based fluid collection without interrupting a fluid connection between the patient and the removable and/or replaceable collection canister or introducing atmospheric air into the fluid pathway.

According to yet another aspect of this invention, a fluid pathway clearing apparatus is provided for a chest drainage system including a collection device and a fluid pathway configured to extend from a patient to the collection device. The fluid pathway has a proximal portion configured to extend proximally toward the patient and a distal portion configured to extend distally from the patient. The apparatus includes an accumulator configured to store sub-atmospheric pressure and configured to be coupled to the chest drain system for providing the sub-atmospheric pressure to the distal portion of the fluid pathway. It also includes a valve configured to be coupled to the proximal portion of the fluid pathway and configured to selectively relieve pressure in the proximal portion of the fluid pathway.

In another aspect of the invention, a method is provided for clearing a fluid pathway of a chest drainage system, the fluid pathway having a proximal portion configured to extend proximally toward the patient and a distal portion configured to extend distally from the patient. The method includes (1) detecting a difference in pressure having a predetermined magnitude between the proximal and distal portions of the fluid pathway; (2) opening a valve to permit release of pressure in the proximal portion of the fluid pathway; (3) introducing sub-atmospheric pressure to the distal portion of the fluid pathway from an accumulator of a pressure source; (4) closing the valve; and (5) ceasing the introduction of sub-atmospheric pressure to the distal portion of the fluid pathway.

In another aspect, the invention provides a chest drainage system including a drainage catheter defining a drainage lumen and at least one drainage opening through which fluid is drawn into the drainage lumen from a pleural cavity. The chest drainage system also includes a suction system coupled to apply suction to the drainage lumen in order to draw fluid into the drainage lumen through the at least one drainage opening, the suction system including a pump, an accumulator in fluid communication with the pump, and a valve coupled between the accumulator and the drainage catheter. The chest drainage system also includes a fluid collector coupled to receive fluid from the drainage lumen of the drainage catheter. The pump is configured to generate a negative pressure in the accumulator, the valve is configured to open when there is a blockage between the pleural cavity and the fluid collector, and the opening of the valve causes the negative pressure in the accumulator to be applied to the drainage catheter such that the blockage is drawn into the fluid collector.

In another aspect, the invention provides a method for monitoring an air leak in a pleural cavity of a patient. The method includes the steps of measuring a rate of pressure decay in the pleural cavity of the patient; correlating the rate of pressure decay to an associated air leak of the pleural cavity of the patient according to the following formula:

$$Q_{Airleak} \alpha \int P dt$$

where:

$Q_{Airleak}$ is an extrapolated air leak

P is a measured pressure t is time; and generating an indicator showing a trend in the magnitude of the air leak of the pleural cavity.

In another aspect of the invention, a chest drainage system is provided that includes a drainage catheter defining a drainage lumen and at least one drainage opening through which fluid is drawn into the drainage lumen from a pleural cavity; a suction system coupled to apply suction to the drainage lumen in order to draw fluid into the drainage lumen through the at least one drainage opening; and a fluid collector coupled to receive fluid from the drainage lumen of the drainage catheter. It also includes a pressure sensor coupled to the suction system and positioned for sensing a pressure in the pleural cavity; a processor coupled to receive a signal from the pressure sensor based on the sensed pressure in the pleural cavity; and a plurality of indicators coupled to the processor and configured to visually indicate a status corresponding to the sensed pressure in the pleural cavity to an operator. The processor is configured to selectively activate the plurality of indicators such that: a first indicator of the plurality of indicators is activated when the sensed pressure is within a first predefined range, a second indicator of the plurality of indicator is activated when the sensed pressure is within a second predefined range, and a third indicator of the plurality of indicators is activated when the sensed pressure is within a third predefined range.

BRIEF DESCRIPTION OF THE DRAWINGS

The invention is best understood from the following detailed description when read in connection with the accompanying drawings. It is emphasized that, according to common practice, the various features of the drawings are not to scale. On the contrary, the dimensions of the various features are arbitrarily expanded or reduced for clarity. Included in the drawings are the following figures.

DETAILED DESCRIPTION OF THE INVENTION

Figure 1:
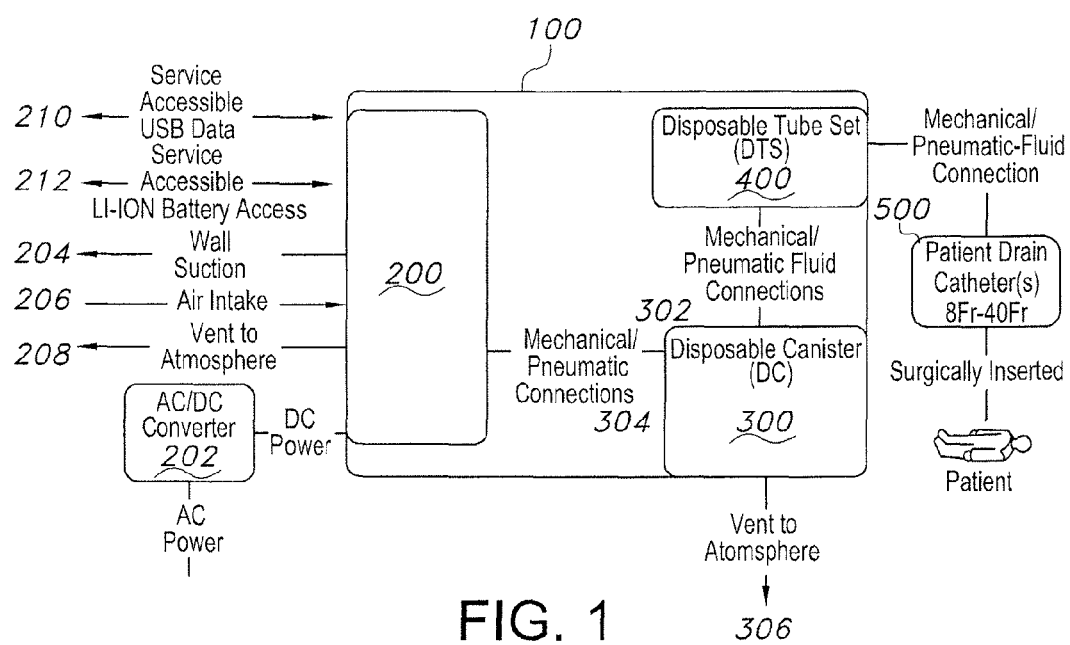
FIG. 1 is a block diagram illustrating an exemplary chest drainage system in accordance with aspects of the present invention.

This invention will now be described with reference to several embodiments selected for illustration in the drawings. It will be appreciated that the scope and spirit of the invention are not limited to the illustrated embodiments. It will further be appreciated that the drawings are not rendered to any particular proportion or scale. Also, any dimensions referred to in the description of the illustrated embodiments are provided merely for the purpose of illustration. The invention is not limited to any particular dimensions, materials, or other details of the illustrated embodiments.

The exemplary systems and methods described herein are usable to drain or otherwise recover fluid from a patient. The systems and methods are described herein primarily with respect to draining the pleural cavity of a patient or to chest drainage for convenience according to embodiments of the invention selected for description and illustration. However, it will be understood by one of ordinary skill in the art that the disclosed systems and methods are not so limited. The disclosed systems and methods may be used to drain fluid from other body cavities such as, for example, the cranial cavity or the peritoneal cavity. Accordingly, this invention applies to a wide variety of medical drainage systems, such as fluid recovery systems, including for example chest drainage systems and those chest drainage systems used as pleural drainage systems.

Generally, chest drainage systems are configured to restore the lungs and pulmonary physiology to their normal condition, by removing air and/or other fluids to help re-establish normal vacuum pressures, lung expansion, and breathing dynamics; to evacuate any pooling fluids and/or air following open heart surgery, thoracic surgery or chest trauma; and/or to facilitate collection of autologous blood from the patient's pleural cavity or mediastinal area for reinfusion purposes in post-operative and trauma blood loss management. The disclosed systems are usable by thoracic surgeons, cardiac surgeons, general surgeons, pulmonary physicians, oncologists, critical care physicians, nurses, home health care professionals, and other health care professionals.

As used herein, the term "patient" refers to an animal to be treated by the disclosed systems and methods. While the systems and methods are described herein primarily with respect to human patients, it will be understood by one of ordinary skill in the art that they are not so limited.

Referring now to the figures, FIG. 1 illustrates an exemplary chest drainage system 100 in accordance with aspects of the present invention. System 100 is usable to drain fluid from the pleural cavity of a patient. As a general overview, system 100 includes a control module 200, a collection device 300, and a fluid pathway 400 that is provided, for example, by a disposable tube set. Additional details of chest drainage system 100 will be provided herein.

Control module 200 houses the electronic components that control chest drainage system 100. Control module 200 is operable to collect and store data about the operation of chest drainage system 100. Control module 200 may be configured to receive power from an external power source (e.g., from an AC power source via AC/DC converter 202). Alternatively or additionally, control module 200 may include an internal power source (e.g., a rechargeable battery). An internal power source may be preferable to increase patient mobility with the chest drainage system 100. Control module 200 may further include a switch, button, or other device for powering control module 200 on and off.

In addition to electrical connection, control module 200 further provides mechanical connections for use in the operation of chest drainage system 100. Control module 200 includes a suction port 204 for receiving suction from an external suction source (e.g., via connection to a wall-mounted suction source). Control module 200 includes an air intake 206 for use in regulating the amount of suction applied by the external suction source. Control module 200 also includes a vent 208 for selectively providing communication with atmosphere. The use of these mechanical connections in operation will be described in further detail herein.

Control module 200 allows the user to set the suction pressure applied by the external suction source. For example, suction pressure may be set from approximately −5 cmH$_2$O to approximately −40 cmH$_2$O, with numerical increments at −5 cmH$_2$O, −10 cmH$_2$O, −15 cmH$_2$O, −20 cmH$_2$O, −30 cmH$_2$O, and −40 cmH$_2$O. Control module 200 may also include an internal suction source for providing suction without an external suction source at, for example, −5, −10, −15, −20 cm H$_2$O. If the system is set to a higher applied suction when the system is disconnected from the external suction source (e.g., to provide mobile suction), the system will automatically adjust the suction pressure to −20 cm H$_2$O. When control module 200 detects that an external suction source is attached, it may be operable to disable suction provided internally and operate using the external suction source for applied suction. Control module 200 may provide a visual notification to the user when suction is being provided internally.

Control module 200 further desirably includes an accessible USB port 210 enabled to support automated system testing, diagnostics, and in-service upgrades. Where control module 200 includes a battery, control module 200 may include a battery access port 212 to enable checking or replacing the battery.

Collection device 300 collects fluid (e.g., gas or liquid or a combination of gas and liquid) drained from the patient. In an exemplary embodiment, collection device 300 is a removable and/or replaceable collection canister. In other words, it is optionally removable, replaceable, or removable and replaceable. Collection device 300 includes an inlet port 302 for received fluid from fluid pathway 400. Collection device 300 further includes a suction port 304 for receiving the suction pressure provided by control module 200. In this way, collection device 300 may be coupled to receive suction from control module 200 and provide suction to fluid pathway 400. Like control module 200, collection device 300 includes a vent port 306 for selectively providing communication with atmosphere. The vent port 306 may be coupled to a relief valve in control module 200 for providing the communication with atmosphere.

Control module 200 may be operable to detect when collection device 300 is full. When control module 200 detects that collection device 300 is full or overflowing, it may provide a visual notification to the user. Chest drainage system 100 may further include a needle-less access connector to allow collected fluid to be withdrawn for testing and analysis. A suitable needle-less access connector will be known to one of ordinary skill in the art.

Collection device 300 may also desirably allow for the visual inspection of collected fluid and have an access line to allow collected blood to be withdrawn from the collection chamber for blood recovery, and allow the trending of volume collected over time by providing a writeable surface on the collection chamber to mark volumes at time increments. In an exemplary embodiment, collection device 300 has a volume of at least approximately 1200 mL. When a chest drainage system is used for pediatric patients, it may be desirable that collection device 300 have a volume of no greater than approximately 200 mL.

Fluid pathway 400 provides a path for fluid from the patient to drain into collection device 300. In an exemplary embodiment, fluid pathway 400 comprises one or more tubes. Fluid pathway 400 may include one tube for draining fluid from the patient into collection device 300. Fluid pathway 400 may also include a second tube for selectively relieving negative pressure in the first tube, as will be described below. Suitable tubes will be known to one of ordinary skill in the art from the description herein.

In operation, fluid pathway 400 is connected to collection device 300. Fluid pathway 400 may then be secured to the patient via a patient drain catheter inserted in the patient (e.g., via patient drain catheter 500). For suction drainage, control module 200 provides suction pressure to collection device 300, thereby coupling the suction to fluid pathway 400. For gravity drainage, gravity is allowed to draw the fluid through fluid pathway 400 and into collection device 300. During operation, control module 200 may monitor and provide visual indications relating to any air leak.

Control module 200 may preferably include a means for the user to mount it to a pole. For example, control module 200 may include hangers for mounting. An exemplary hanger system is disclosed in U.S. Pat. No. 7,232,105, which is incorporated herein by reference. Additional structures and equivalent structures for mounting control module 200 to a vertical pole or horizontal rail will be apparent to those of skill in the art from the description herein.

Control module 200 may also include a handle. An exemplary ornamental design of a handle system is disclosed in U.S. Pat. No. D517,897, which is incorporated herein by reference.

During drainage of fluid from a patient, a dependent loop of tubing may occur when a portion of the tubing forms a U-shape that requires fluid in the tube to flow against gravity to reach the distal end of the tube. With drainage systems, gravity is an important factor affecting fluid flow into the collection device. As the vertical distance between the patient and the collection device increases, fluid flow increases as well. Fluid collected in a dependent loop in the drainage tubing can stop flow completely.

Accordingly, a chest drainage system according to aspects of this invention detects the state at which there is the presence of a dependent loop. Then, the system applies more negative pressure to the front (closer to the collection device) of the fluid trapped in the fluid pathway that is in a more distal portion of the fluid pathway, while allowing pressure to be relieved in the back (closer to the patient) of the fluid trapped in the fluid pathway at a location that is in a more proximal portion of the fluid pathway. This creates a pressure differential that causes air and/or other fluids trapped in the tubing to move towards the sub-atmospheric pressure very rapidly in order to stabilize the system. For example, although the invention is not limited to any specific time within which the system is stabilized or trapped fluid is removed, the pressure differential is preferably applied for less than 15 seconds, more preferably less than 5 seconds, and most preferably less than 2 seconds. It should be appreciated that this amount of time is influenced by various factors including, for example, the magnitude of the pressure charge in the accumulator, the viscosity of fluid forming the blockage, the diameter of the drainage tube and other tubing of the system, any possible kinks or defects in the tubing, the amount of applied pressure, the volume of the blockage, and any restrictions attributable to the system connectors.

The negative pressure applied to the front or distal portion of the tubing may be created, e.g., through the utilization of a vacuum pump, to draw down the pressure in a pressure storage device such as a pressure accumulator. While the accumulator is being charged with negative pressure, it is isolated from the rest of the chest drain via a valve. The accumulator may optionally be a distinct, discrete component from the rest of the drainage system, or may be an integral part of the drainage system.

After a predetermined amount of negative pressure is achieved in the accumulator, the valve may then be opened and the negative pressure exposed to the rest of the chest drain, and subsequently to the distal side of the fluid trapped in the tubing. In order to maximize the movement of fluid trapped in the tubing, another valve may be activated that opens the back end or proximal portion closer to the patient to allow air to be drawn into the system, thus relieving the negative pressure charge that clears the dependent loop.

The system is desirably operable to detect a fully or partially blocked or kinked pneumatic fluid pathway based on an algorithm that considers one or more of elapsed time, pressure differential in the fluid pathway, and predetermined time delay settings. Such blockage may include, or be the result of the presence of, solids, semi-solids, liquids, gases, or combinations of the foregoing in the fluid pathway that induce a registered pressure differential, which actuates the pathway clearing function.

The fluid pathway may be a tube, for example, such as a flexible, polymeric material. The fluid pathway may have a single lumen or multiple lumens. During clearing of the fluid pathway, the accumulator's negative pressure is used to evacuate at least some or, more preferably, substantially all of the blockage that induced the pressure differential, recognizing that the tube will typically have residual material remaining. In one exemplary embodiment, the fluid pathway can be considered to be "cleared" at the point when the system is able to restore differential pressure to a point below a predetermined pressure differential threshold.

When the system detects a dependent fluid loop that generates a predetermined pressure differential (e.g., 10 cmH$_2$O) between the patient and the canister or collection device, the system can clear the dependent fluid loop. In one embodiment, the system can clear the dependent fluid loop up to half of the patient tubing set length.

The system includes a pressure accumulator to store sub-atmospheric pressure and apply a negative pressure to the fluid pathway downstream or distal of a blockage that creates a differential across the dependent fluid loop, preferably while substantially maintaining prescribed sub-atmospheric pressure at the patient, and preferably without applying a positive pressure to the blockage and without using a mechanical clearing device.

According to a preferred embodiment, the pressure to clear the fluid pathway is created independent of the collection chamber, which provides a space for the collection of fluid, and is then introduced to the collection chamber. It is believed that such a system is superior to a system that incrementally applies small pressures to the chamber, checks, and iterates, because such a system may not adequately clear the patient tube quickly or effectively as the residual pressure in the collection chamber is transferred to the patient. Also, because airflow is extrapolated from pump work, such a system may require close control of a vent valve during blockage clearing so it is not interpreted as a patient leak.

Additionally, preferred embodiments of the system do not use positive pressure to unclog a blockage by building up pressure and pumping the clog. Although positive pressure is alternatively used, it is advantageous according to preferred aspects of the invention to use sub-atmospheric pressure, introduced distally of a blockage, to generate a pressure differential sufficient to "pull" a blockage in a direction away from the patient. Doing so reduces the risk of exposing the patient to positive pressure and also eliminates the need for mechanisms (e.g., valves) in the drainage line to prevent such exposure. Also, the use of sub-atmospheric pressure permits continued measurement of pressure and substantially continuous application of sub-atmospheric pressure to the patient.

The system includes a vent to introduce air into the fluid pathway upstream or proximal of a blockage to prevent build up of sub-atmospheric pressure. In other words, the vent provides a vent to relieve the negative pressure charge across the pressure differential; thereby, moving the fluid. Although it is not its primary function, the vent may also prevent build up of sub-atmospheric pressure in the fluid pathway. Also, relieving the negative pressure charge in sequence is preferably optimized such that interruptions or variations of the applied negative pressures to the patient are minimized (e.g., less than such interruptions and variations that may be typically caused by manual manipulation of a tube to move a blockage such as by lifting the tube).

A blockage is cleared within a shortened, predetermined period of time. This feature is beneficial in that it provides a means to quickly clear the tube while applying less pressure than would be applied by manual manipulation of the tube to remove a blockage. More specifically, it has been discovered that the use of a source of sub-atmospheric pressure permits rapid clearing of a tube using moderate pressure differentials. It also permits control of the clearing time and differential pressure magnitudes.

Figure 2:
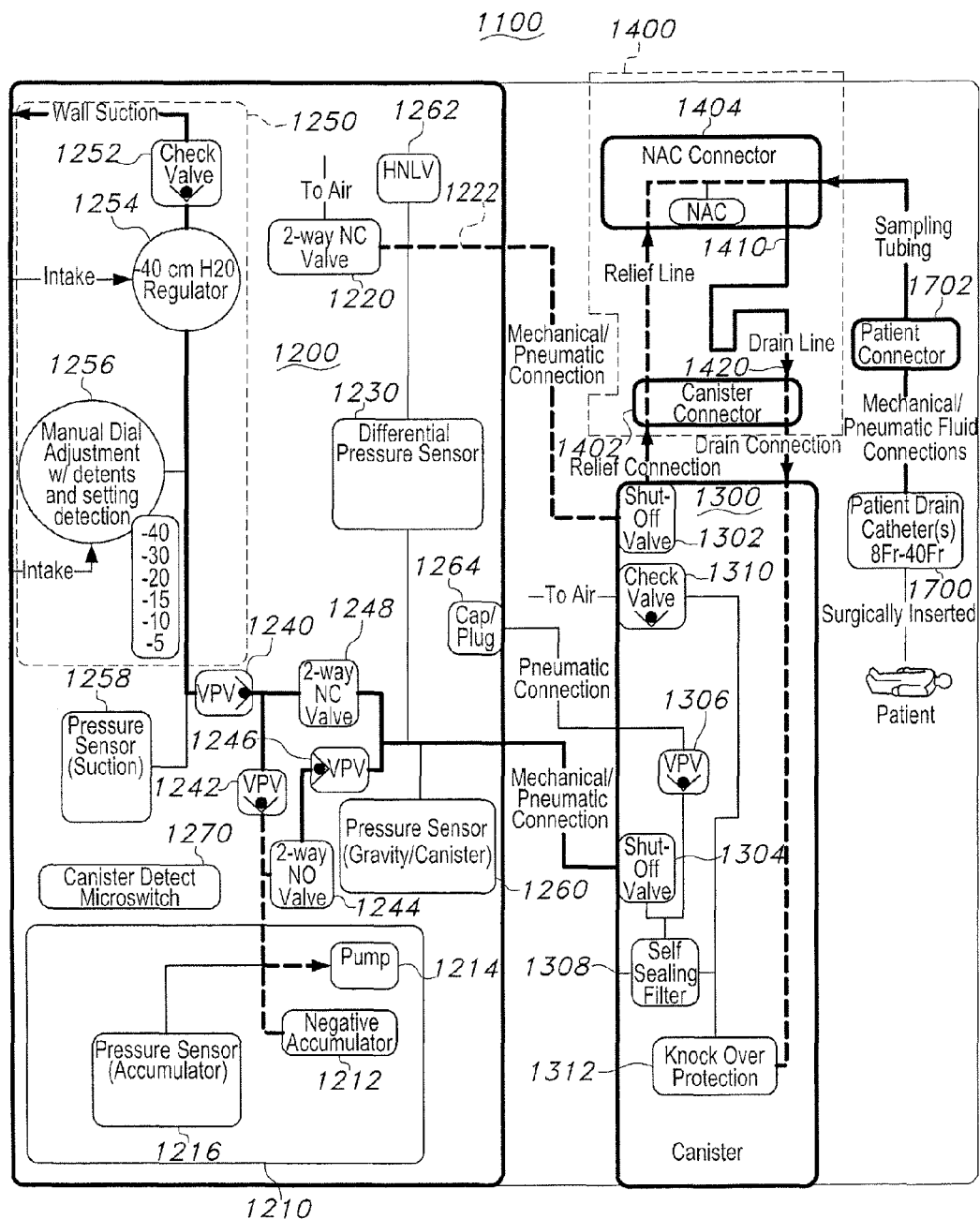
FIG. 2 is a schematic diagram illustrating another exemplary chest drainage system in accordance with aspects of the present invention.

With reference to the drawings, FIG. 2 illustrates another exemplary chest drainage system 1100 in accordance with aspects of the present invention. System 1100 is usable to drain fluid from the pleural and/or mediastinal cavity of a patient. As a general overview, system 1100 includes a control module 1200, a collection device 1300, and a fluid pathway 1400. Additional details of chest drainage system 1100 will be provided herein.

Control module 1200 houses the electronic components of system 1100. Control module 1200 may include any or all of the features described above with respect to control module 200. Collection device 1300 collects fluid drained from the patient. Collection device 1300 may include any or all of the features described above with respect to collection device or canister 300.

Fluid pathway 1400 provides a path for fluid from the patient to drain into collection device 1300. Fluid pathway 140Q is configured to extend from collection device 1300 to the patient. Fluid pathway has a portion 1410 configured to extend proximally toward the patient and a portion 1420 configured to extend distally from the patient. As used herein, the terms "proximal portion" and "distal portion" are not limited to any particular section or length of the fluid pathway. To the contrary, the terms "proximal portion" and "distal portion" of the fluid pathway are relative terms meant to describe portions of the fluid pathway that are proximal or distal, respectively, of a fluid pathway portion that may become at least partially blocked during use.

Chest drainage system 1100 includes means for substantially clearing a blockage in fluid pathway 1400 that may form between the proximal portion 1410 and the distal portion 1420. The means for substantially clearing a blockage in a fluid pathway may include the structures set forth below, and any other known means for substantially clearing a blockage in a fluid pathway. For example, the means can include a positive or negative pressure supply, a source of fluid flow, an apparatus for manipulating the elevation of the fluid pathway, an apparatus for mechanically promoting movement of a blockage (e.g., by radial or axial movement with respect to the fluid pathway), etc. Additional structures and equivalent structures will be apparent to those of skill in the art.

Control module 1200 includes a pressure source 1210. According to a preferred aspect of this invention, the pressure source 1210 includes means for pressure storage. For example, it may include pressure storage that stores a finite volume of pressurized fluid such as sub-atmospheric gas as opposed to a continuous or substantially unlimited source of pressure. In other words, such pressure storage can be configured to hold a discrete "charge" of sub-atmospheric pressure as an alternative to a continuous or other source of sub-atmospheric pressure that may provide a relatively unlimited source of sub-atmospheric pressure. For example, although the pressure source may optionally include hospital wall suction as a substantially continuous source of sub-atmospheric pressure according to aspects of this invention, it is advantageous according to embodiments of this invention to utilize a pressure source including a pressure storage configured to store a discrete volume of pressurized fluid. According to one exemplary embodiment, the pressure source includes an accumulator that is configured to store pressure at least temporarily. Additional structures and equivalent structures for storing pressure will be apparent to those of skill in the art from the description herein.

Pressure source 1210 is configured to selectively provide sub-atmospheric pressure to the distal portion 1420 of the fluid pathway 1400. Pressure source 1210 may be operable to provide continuous sustained suction pressure, for example, when system 1100 is not connected to an external suction source. Alternatively, pressure source 1210 may be operable to provide one or more pulses of sub-atmospheric pressure. Pressure source 1210 may provide sub-atmospheric pressure to the distal portion 1420 of the fluid pathway 1400 via the collection device 1300 and may be coupled directly to collection device 1300.

In an exemplary embodiment, pressure source 1210 comprises a pressure accumulator 1212 and means for generating sub-atmospheric pressure 1214. Pressure accumulator 1212 is configured to store sub-atmospheric pressure. The stored sub-atmospheric pressure can then be introduced to, or fluidly coupled to, fluid pathway 1400. In an exemplary embodiment, pressure accumulator 1212 is a sealed pressure vessel that is pneumatically connected in circuit with a means for generating pressure and a valve where one side of the valve is connected to the collection device 1300 and the other side of the valve is connected to the accumulator 1212. This allows the means for generating pressure 1214 to negatively charge the accumulator to negative pressures (e.g., −700 cm $H_2O$). When it is configured to store negative pressure or sub-atmospheric pressure, the accumulator may be referred to as a negative accumulator. Also, although the pressure source may alternatively be the primary source of suction for applying sub-atmospheric pressure for chest drainage, the pressure source according to exemplary embodiments of the invention is separate from and supplemental to the primary source of suction, which may be a wall suction source that is regulated for applying sub-atmospheric pressure to the drainage line. Accordingly, the accumulator component of the pressure source is, according to exemplary embodiments, a component of the pressure source that is distinct from, and/or is operable independently from, the wall suction source or other primary suction source.

The size of the pressure accumulator may be selected based on the empty volume of the collection device 1300 and all pneumatic pathways up to and perhaps beyond the point of the distal end of the dependent loop. Desirably, the pressure source 1210 is able to clear a dependent fluid loop in one sequence. Therefore, the size of the pressure accumulator should be selected so that it is large enough in size and strength to hold a negative charge that when released into the collection device 1300, it temporarily increases the negative pressure in the canister to a level that is able to successfully pull the blockage into the collection device 1300. For example, if the distance to the top of the collection device is 50 cm and the length of the fluid pathway 1400 allows the blockage to be positioned 20 cm below the collection device 1300, then the resulting canister pressure after an accumulator release should be at least approximately −70 cm $H_2O$ in order suck the blockage into the canister.

Pressure accumulator 1212 may be constructed of plastic (e.g., ABS). Alternatively, pressure accumulator 1212 can be constructed of many different polymers, metals or other suitable materials, as the pressure levels required for chest drainage are typically not that high. In one exemplary embodiment, the accumulator 1212 is optionally constructed of two or more separate injection molded pieces of plastic and welded together (via ultrasonic welding or other means) in order to ensure that the accumulator is a sealed pressure vessel.

Means for generating sub-atmospheric pressure 1214 is operable to charge pressure accumulator 1212, i.e. generate the sub-atmospheric pressure stored in pressure accumulator 1212. Means for generating sub-atmospheric pressure 1214 may be, for example, a pump or a connection with an external suction source. Suitable pumps for use as pressure generating means 1214 include, for example, a diaphragm pump such as a diaphragm pump available from Gardner Denver Thomas Division, of Sheboygan, Wis. (e.g., Part No. 1410D/BLOC), although other diaphragm pumps and other types of pumps are optionally used. Other means for generating sub-atmospheric pressure 1214 will be known to one of ordinary skill in the art from the description herein. Pressure source 1210 may further include a sensor 1216 for measuring the pressure stored in pressure accumulator 1212.

Figure 2A:
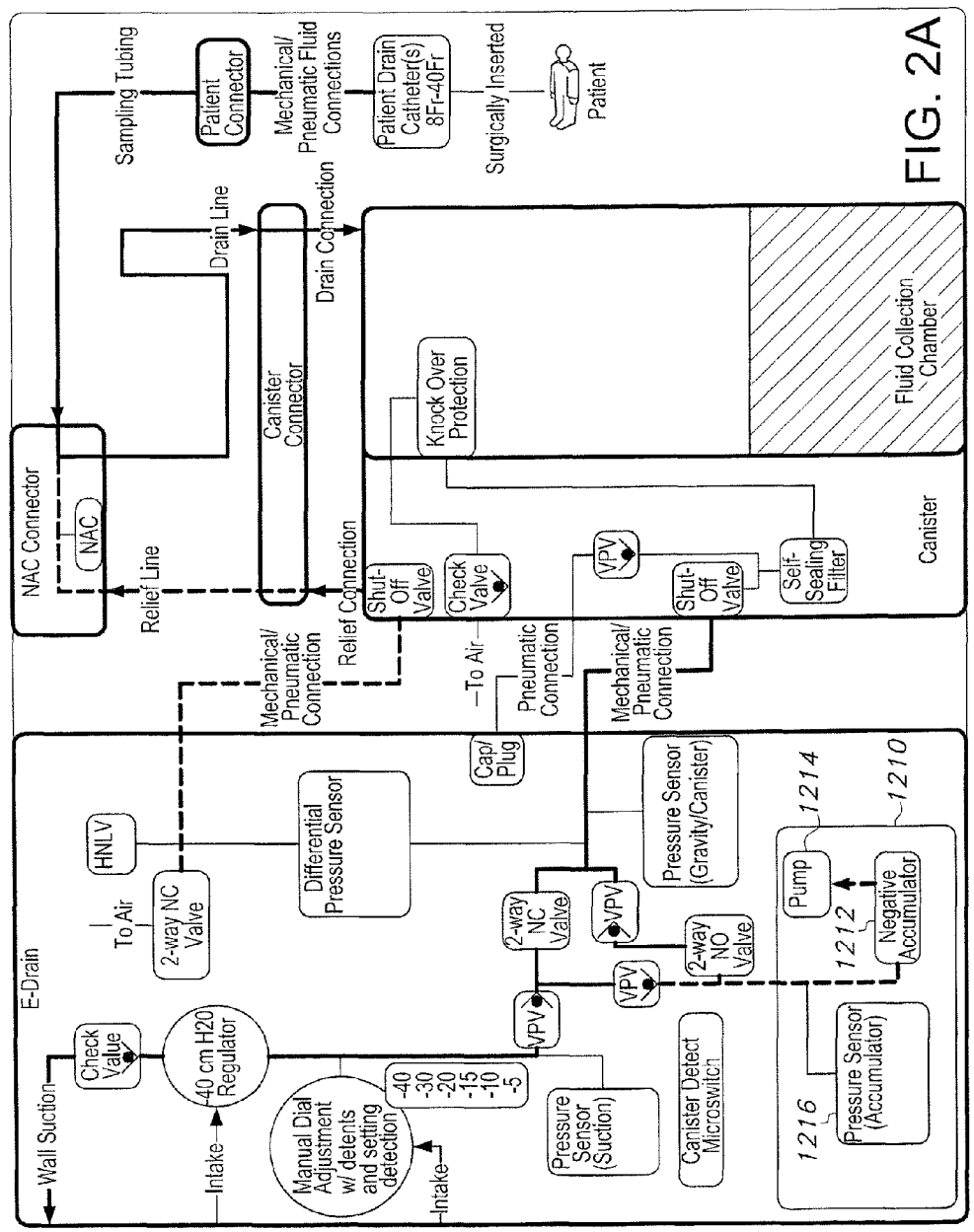
FIG. 2A is a schematic diagram illustrating an optional modification to the chest drainage system of FIG. 2.

It will be understood by one of ordinary skill in the art from the description herein that the connection between pressure accumulator 1212 and means for generating sub-atmospheric pressure 1214 shown in FIG. 2 is illustrative and not limiting. For example, as shown in FIG. 2A, pressure accumulator 1212 and means for generating sub-atmospheric pressure 1214 may be connected in series as opposed to the "T" connection illustrated in FIG. 2.

Control module 1200 also includes a valve 1220 such as a 2-way valve in the normally closed position. Valve 1220 is in fluid communication with the proximal portion 1410 of fluid pathway 1400. Valve 1220 may establish this fluid communication via a separate vent line 1222. Valve 1220 is configured to selectively relieve pressure in the proximal portion 1410 of fluid pathway 1400 by selectively coupling the proximal portion 1410 with open air. Control module 1200 controls the opening and closing of valve 1220. In operation of system 1100, valve 1220 is normally closed.

Chest drainage system 1100 also includes means for determining when to actuate the above-described clearing means.

The means for determining when to actuate the above-described clearing means may include the structures set forth below, and any other known means for determining when to actuate the above-described clearing means. For example, the means can include a controller, a sensor, a timer, or a combination of the foregoing. Additional structures and equivalent structures will be apparent to those of skill in the art.

Control module 1200 also includes a differential pressure sensor 1230. Differential pressure sensor 1230 measures a pressure difference between the proximal portion 1410 and the distal portion 1420 of the fluid pathway 1400. To measure the pressure at the proximal portion 1410, sensor 1230 may measure the pressure in vent line 1222. To measure the pressure at the distal portion 1420, sensor 1230 may measure the pressure in collection device 1300. Control module 1200 may use the pressure measured by sensor 1230 to determine when to actuate pressure source 1210 and valve 1220, as will be described below.

The operation of chest drainage system 1100 will now be described with reference to FIGS. 3A-3E. As chest drainage system 1100 is used to drain fluid from a patient, there is a possibility that the fluid may form a complete or partial blockage in fluid pathway 1400. The blockage may inhibit further drainage of fluid from the patient. Accordingly, it is desirable to promptly remove blockages from fluid pathway 1400.

Figure 3A:
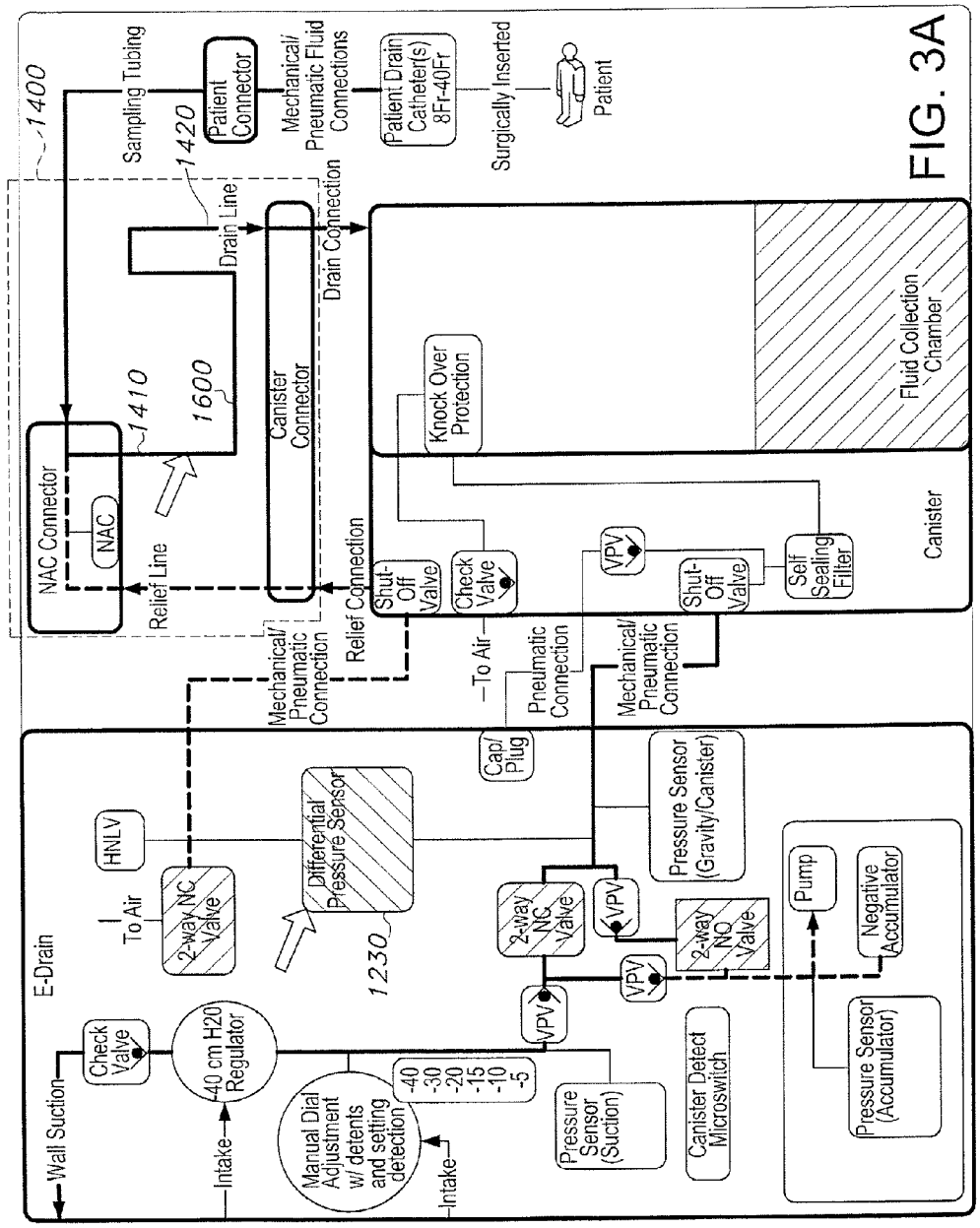
FIGS. 3A-3E are schematic diagrams illustrating the operation of the chest drainage system of FIG. 2.

As shown in FIG. 3A, control module 1200 detects a blockage 1600 in fluid pathway 1400 using differential pressure sensor 1230. When there is a blockage 1600 in fluid pathway 1400, a difference in pressure will be generated between the distal portion 1420 (where suction pressure is applied) and the proximal portion 1410 (where the suction pressure cannot adequately reach). Accordingly, differential pressure sensor 1230 will detect a difference in pressure between proximal portion 1410 and distal portion 1420 in the event that a blockage 1600 of fluid pathway 1400 occurs. Blockage 1600 may generate a difference in pressure as small as 1 cm $H_2O$ or greater, even less under some circumstances.

For example, a blockage itself may generate a difference in pressure of any amount from greater than 0 to a greater differential based on the limits of the system. If for example a column of fluid is 10 cm tall and the collection chamber and tube set system only allow a maximum of 10 cm height from the bottom-most point of the tubing to the top of the collection chamber, then the greatest pressure differential would be expected to be about 10 cm. Alternatively, if a chest drain is approximately 30 cm tall and the tubing is 72 inch in length, the bottom most portion of the tubing may be 24 inches below the drain, for example, if the drain is hanging on a hospital bed rail. Therefore, factors such as the maximum differential pressures that can be generated and the maximum column of fluid that could be collected in the tube would impact the overall optimization and requirements of an accumulator profile (e.g., its volume and charge) in order to be able to remove a blockage in one or more discharges of the accumulator.

For example, and for purposes of illustration only, a −5 cm negative pressure generated in pressure source 1210 may be sufficient to clear a 5 cm tube blockage, and a −10 cm negative pressure may be sufficient to clear a 10 cm tube blockage, etc. Such negative pressures can have a wide range, including from −5 to −80 cm for example. For example, an accumulator having a volume of 300 cc may be charged by a pump to a negative −500 $cmH_2O$. Upon releasing such a charge into a collection canister, the residual pressure in the canister achieves a negative pressure that is more negative than the total head height of the blockage (e.g., 14 cm $H_2O$). This would result in a successful clearing of fluid in the tube. As the fluid clears into the collection chamber the negative pressure charge of the canister becomes more positive due to equalization of pressures caused by movement of the blockage; therefore, it is preferable to achieve a residual negative charge in the canister of at least the height of the blockage, and the system should accommodate for the pressure change as the fluid is cleared in addition to a sufficient excess charge to ensure that the blockage removal is maximized.

Figure 3B:
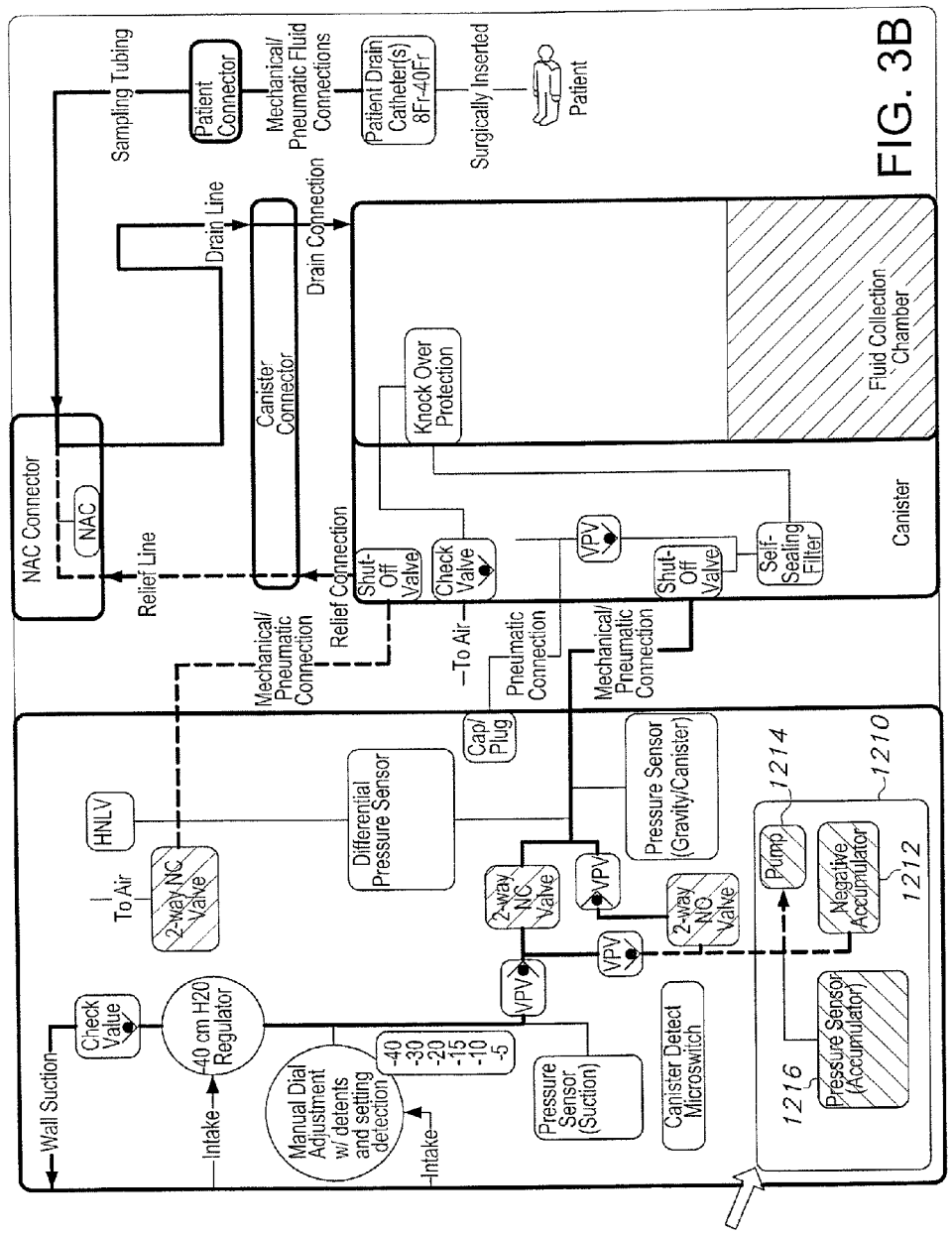
Figure 3C:
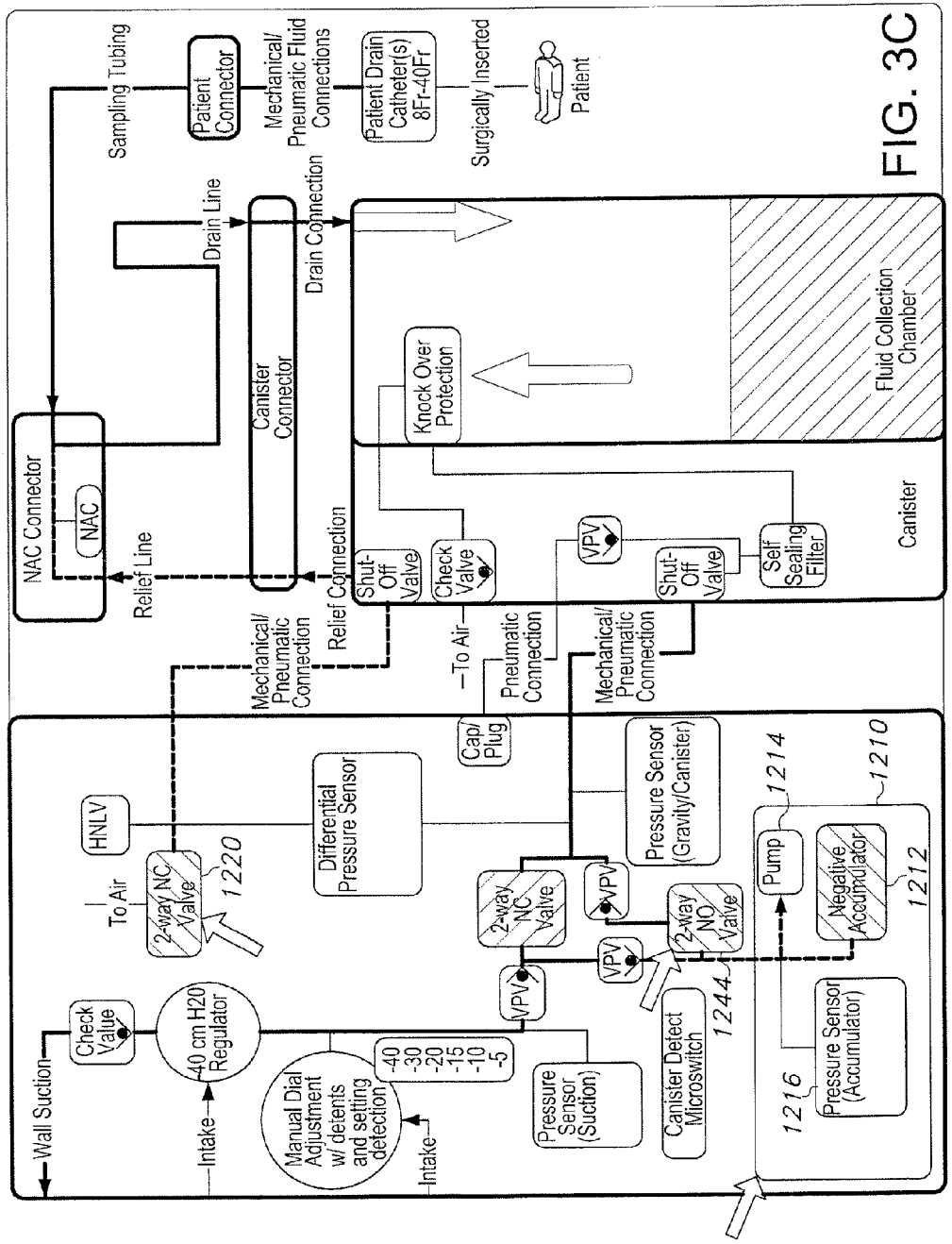

In accordance with aspects of the present invention, control module 1200 is programmed to clear the blockage 1600 when the differential pressure meets or exceeds a predetermined magnitude. When a predetermined pressure differential is detected between the proximal portion 1410 and the distal portion 1420 of the fluid pathway, control module 1200 is configured to generate sub-atmospheric pressure in pressure source 1210, as shown in FIG. 3B. When a sub-atmospheric pressure having sufficient magnitude (e.g., a magnitude sufficient to remove a particular blockage) is generated in pressure source 1210, control module 1200 couples pressure source 1210 with the distal portion 1420 of the fluid pathway via valve 1244, and opens valve 1220, as shown in FIG. 3C.

Figure 3D:
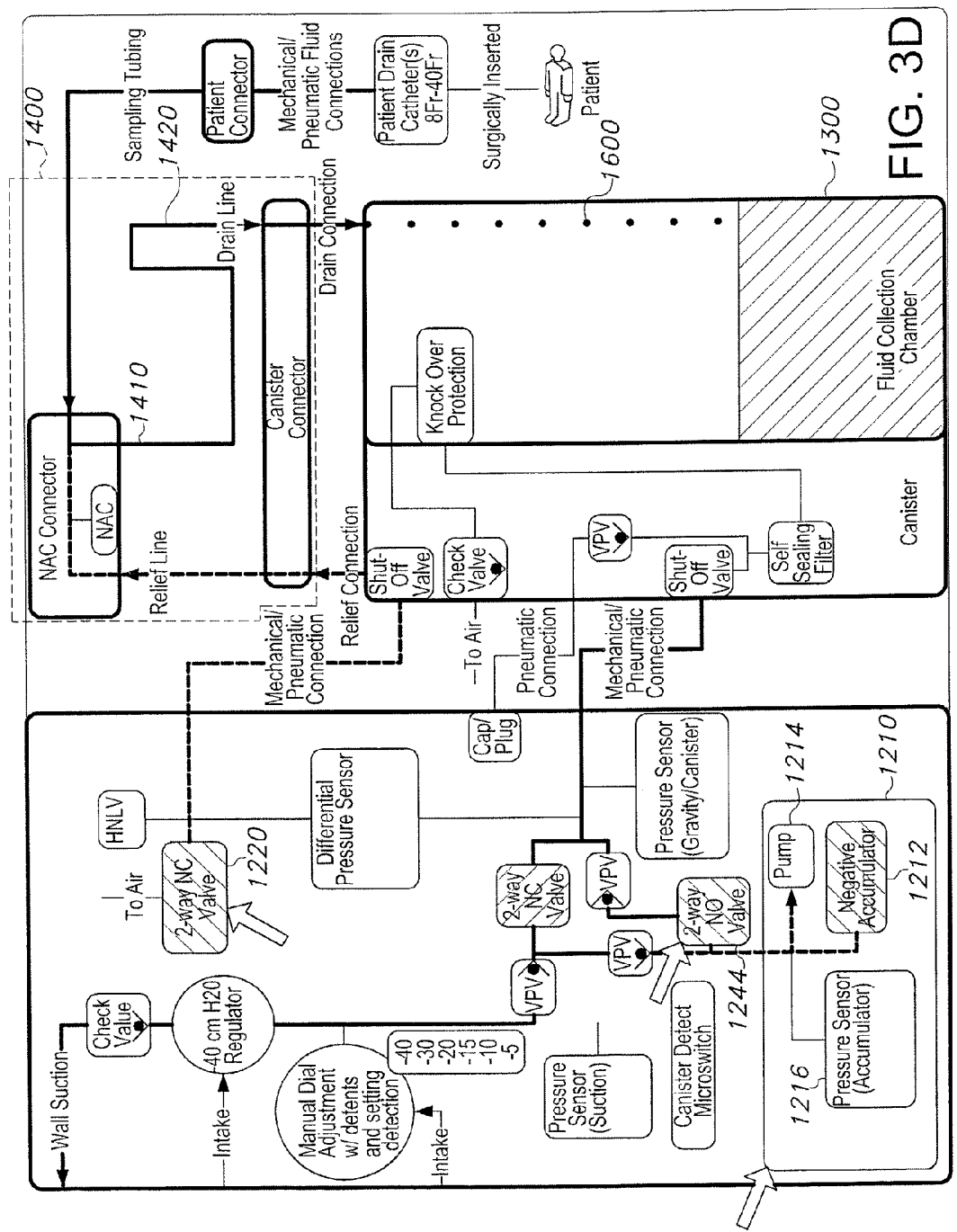

The sub-atmospheric pressure from pressure source 1210 then sucks the blockage 1600 in fluid pathway 1400 into collection device 1300, thereby clearing fluid pathway 1400 to continue draining fluid from the patient, as shown in FIG. 3D. The opening of valve 1220 prevents the sub-atmospheric pressure from pressure source 1210 from being applied to the patient.

Figure 3E:
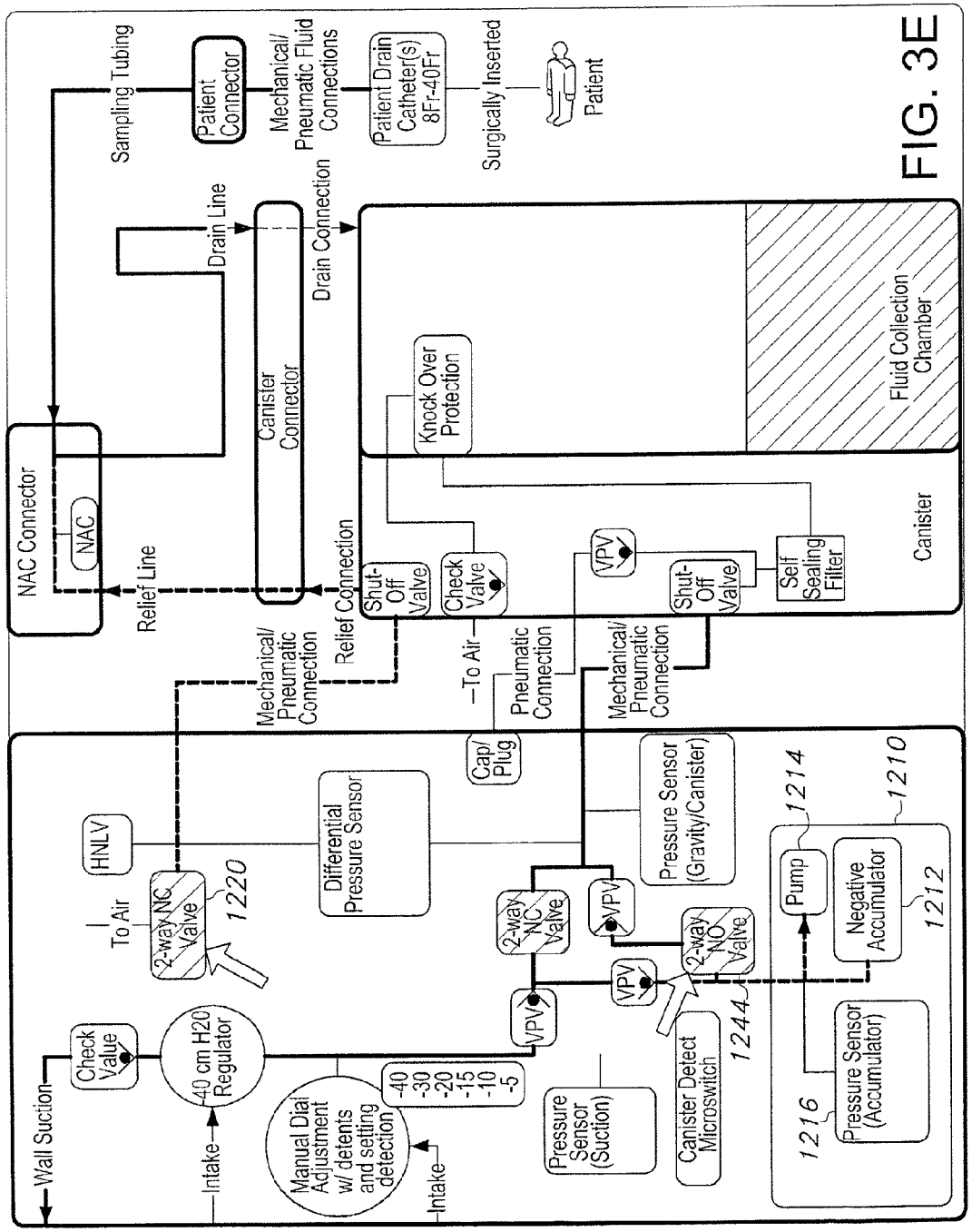

When the blockage 1600 is sufficiently drained, control module 1200 decouples pressure source 1210 from fluid pathway 1400 using valve 1244, and closes valve 1220, as shown in FIG. 3E. Preferably, control module 1200 may be configured to decouple pressure source 1210 when the pressure differential drops below a predetermined point, or after a predetermined period of time.

While control module 1200 is described above as clearing a blockage based on the differential pressure measured by sensor 1230, it is not so limited. Control module 1200 may be additionally or alternatively configured to clear a blockage or clear the fluid pathway 1400 based on elapsed time of operation of chest drainage system 1100.

Pressure source 1210 provides pressure to collection device 1300 using a network of valves 1240, 1242, 1244, 1246, 1248. Valves 1240, 1242, and 1246 may desirably be vacuum protection valves. When suction is applied to fluid pathway 1400 from an external suction source, the suction pressure is applied via valves 1240, 1242, 1244, 1246. Valve 1248 is normally closed during operation.

When pressure source 1210 is coupled to fluid pathway 1400, the sub-atmospheric pressure is applied via valves 1244 and 1246. Valves 1240 and 1242 remain closed as long as the pressure from pressure source 1210 is below (i.e. more negative than) the pressure applied by the external suction source. When the pressure from pressure source 1210 is above (i.e. less negative than) the pressure applied by the external suction source, valves 1240 and 1242 reopen, and normal suction pressure is applied to fluid pathway 1400 from the external suction source. In this way, even when control module 1200 clears a blockage from fluid pathway 1400, the system 1100 substantially maintains a prescribed pressure at the patient when valve 1220 is opened and pressure source 1210 is coupled to fluid pathway 1400. Suitable valves for use as valves 1240, 1242, 1244, 1246, or 1248 will be known to one of ordinary skill in the art from the description herein.

Control module 1200 may further include a pressure regulation system 1250. Pressure regulation system 1250 is operable to regulate the pressure provided by an external suction source. As shown in FIG. 2, pressure regulation system 1250 may include a check valve 1252, a pressure regulator 1254, and a pressure setting mechanism 1256. Check valve 1252 is operable to prevent air from flowing into control module 1200. Pressure regulator 1254 is operable to limit a maximum suction provided by the external suction source. For example, pressure regulator 1254 may limit suction to a maximum of −40 cm H$_2$O. Pressure setting mechanism 1256 enables a user to vary the applied suction pressure up to a maximum regulated suction value. For example, and for purposes of illustration, the setting mechanism may allow variable adjustment of applied suction pressure from −1 cm H$_2$O to a maximum of −40 cmH$_2$O. The suction pressure may be any predetermined pressure between 0 and the maximum allowed by pressure regulator 1254. In an exemplary embodiment, pressure setting mechanism 1256 is a mechanical dial. Suitable components for pressure regulation system 1250 will be known to one of ordinary skill in the art from the description herein.

As illustrated in FIG. 2, control module 1200 may also include a pressure sensor 1258 for sensing the suction pressure provided by pressure regulation system 1250. Control module 1200 may also include an additional pressure sensor 126Q for sensing a pressure at the output of control module 1200.

Control module 1200 may also include a high negativity limit valve 1262. In an exemplary embodiment, high negativity limit valve 1262 is a one-way valve that is activated (or opened) when the pressure reaches a certain limit. For example, if high negative pressure exceeds the mechanical or electronically predetermined limits of the spring forces that keep the high negative limit valve shut, then the valve will open and "relieve" the negative pressure until the pressure is once again under the mechanical limits where the spring forces would close the valve shut. This type of valve can be designed in several ways mechanically in order to achieve the effect of opening when certain pressure limits are reached, as would be understood by one of ordinary skill in the art. For example, the valve optionally includes a spring loaded shut off plunger.

Control module 1200 may also include a sealing element 1264. Sealing element 1264 may be configured to cap, plug, or otherwise partially or fully seal a pneumatic connection between control module 1200 and collection device 1300. In an exemplary embodiment, collection device 1300 is operable to vent out positive pressure through one or more check valves when the collection device 1300 is not loaded in the control module 1200. One check valve may be designed to open at very low pressures. Another check valve may be designed to open at a higher pressure (e.g., >+2.0 cm H$_2$O). This may be desirable because it allows positive pressure to be pushed through the control module 1200 and be measured by pressure sensors. However, this can only be achieved if the valve designed to open at very low pressures is plugged when it is loaded into the control module 1200. Accordingly, when collection device 1300 is coupled to control module 1200, the low-opening valve couples with the sealing element.

Collection device 1300 may also include a shut-off valve 1302. In an exemplary embodiment, shut-off valve 1302 comprises a spring-loaded plunger that seals off the flow paths when the collection device 1300 is not loaded in the control module 1200. When the collection device 1300 is loaded into the control module 1200, the ports of the control module 1200 push the spring-loaded plunger, thereby opening the valve 1302 and allowing flow from the collection device 1300 into the control module or vice versa. This specific shut-off valve 1302 provides the flow path between the electronically controlled relief valve 1220 and the relief flow path to the proximal end 1410 of the fluid pathway 1400.

Collection device may also include a shut-off valve 1304. Shut-off valve may be configured to seal a connection between control module 1200 and collection device 1300. In an exemplary embodiment, shut-off valve 1304 comprises a shut-off valve similar to that described above with respect to shut-off valve 1302. Shut-off valve 1304 provides the flow path for the control module 1200 to measure the pressure within collection device 1300 as well as allow negatively applied pressure to be applied via an external suction source or via pressure source 1210.

Collection device 1300 may also include a vacuum pressure valve 1306, which is described in U.S. Pat. No. 6,358,218, the contents of which are hereby incorporated in their entirety. In an exemplary embodiment, vacuum pressure valve is a one-way check valve, similar to a standard umbrella valve; however, there is no stem, but just a floating disc design that only allows flow in one direction. The top of the floating disc is retained by mechanical features that ensure activation and position.

Collection device 1300 may also include a self-sealing filter 1308. In an exemplary embodiment, self-sealing filter 1308 is a gas or liquid permeable material that seals when exposed to water.

Collection device 1300 may also include a check valve 1310. Check valve 1310 is a valve similar to vacuum pressure valve 1306.

Collection device 1300 may also include a means for knock-over protection 1312. In an exemplary embodiment, knock-over protection means 1312 is a nozzle that is suspended in the middle of the collection device volume. By positioning the nozzle in the middle of the collection chamber volume, it provides a tortuous path for the fluid to migrate into that exit. Additional structures and equivalent structures for knock-over protection will be apparent to those of skill in the art from the description herein.

Fluid pathway 1400 may also include a distal connector 1402. Distal connector 1402 connects the body of the fluid pathway 1400 (e.g., a drain tube) to the collection device 1300. Accordingly, distal connector 1402 is positioned at an end of the distal portion 1420 of the fluid pathway 1400. Suitable connectors for use as distal connector 1402 will be known to one of ordinary skill in the art from the description herein.

Fluid pathway 1400 may also include a proximal connector 1404. Proximal connector 1404 connects the body of the fluid pathway 1400 (e.g., a drain tube) to the patient (e.g., via patient connector 1702 and patient drain catheter 1700). Accordingly, proximal connector 1404 is positioned at an end of the proximal portion 1410 of the fluid pathway 1400. In an exemplary embodiment, proximal connector 1404 is a needle-less access connector. Suitable connectors for use as proximal connector 1404 will be known to one of ordinary skill in the art from the description herein.

Figure 4:
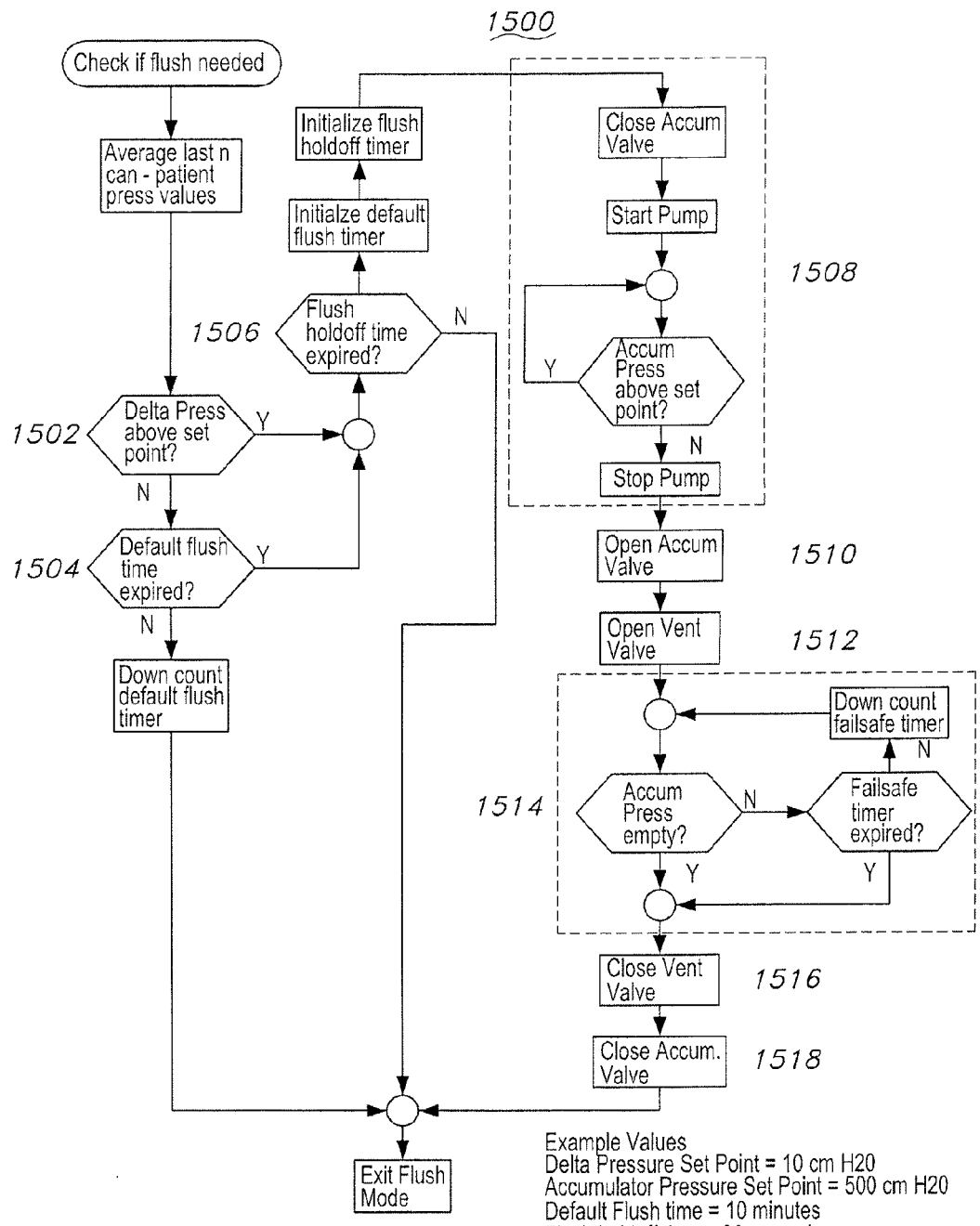
FIG. 4 is a flow chart illustrating an exemplary algorithm for clearing a fluid pathway in accordance with aspects of the present invention.

FIG. 4 is a flow chart illustrating an exemplary method 1500 for clearing a fluid pathway in accordance with aspects of the present invention. For the purposes of illustration, the steps of the method will be described with reference to the components of system 1100.

In step 1502, the differential pressure is checked. In an exemplary embodiment, control module 1200 checks the differential pressure between the proximal portion 1410 and the distal portion 1420 of the fluid pathway 1400. Desirably, ahead of step 1502, control module 1200 may determine an average pressure at each of the proximal portion 1410 (e.g., the patient side) and the distal portion 1420 (e.g., the canister side) over a predetermined period of time. Control module

1200 may then determine the difference between these average pressures to obtain the differential pressure.

If the differential pressure is less than a predetermined magnitude, method 1500 proceeds to step 1504. If the differential pressure is equal to or greater than a predetermined magnitude, method 1500 proceeds to step 1506.

In step 1504, the default timer is checked. In an exemplary embodiment, control module 1200 determines how much time has elapsed since fluid pathway 1400 was last flushed. If a predetermined amount of time has elapsed, method 1500 proceeds to step 1506. If not, control module 1200 determines that it is not necessary to clear fluid pathway 1400 at this time, and method 1500 concludes.

In step 1506, the flush hold-off timer is checked. In an exemplary embodiment, control module 1200 may maintain a flush hold-off timer for determining whether a fluid pathway clearance event should be delayed. If the timer has not reached zero, then control module 1200 determines that the fluid pathway clearance event should be delayed, and method 1500 concludes. If the timer reaches zero, then it is reset, and method 1500 proceeds to step 1508.

In step 1508, the accumulator is charged. In an exemplary embodiment, means for generating pressure 1214 generates a sub-atmospheric pressure for storage in pressure accumulator 1212. When the accumulated sub-atmospheric pressure reaches a predetermined magnitude (e.g., −40 cm $H_2O$), the pressure generating means 1214 may be stopped.

In step 1510, the pressure source is coupled for fluid flow to the fluid pathway by opening an accumulator valve. In an exemplary embodiment, control module 1200 couples pressure source 1210 to the distal portion 1420 of fluid pathway 1400. Pressure source 1210 may be coupled to provide pressure directly to collection device 1300.

In step 1512, the vent valve is opened. In an exemplary embodiment, control module 1200 opens valve 1220 to permit release of pressure in the proximal portion 1410 of fluid pathway 1400.

In step 1514, the blockage is cleared. In an exemplary embodiment, control module 1200 allows the pressure from pressure source 1210 to clear the blockage from fluid pathway 1400. When the sub-atmospheric pressure from pressure source 1210 is depleted, method 1500 advances to step 1516.

Additionally, control module 1200 may monitor the length of time pressure source 1210 is coupled to the distal portion 1420 of fluid pathway 1400. If pressure source 1210 is coupled to the distal portion 1420 for a predetermined length of time, and the sub-atmospheric pressure has not been depleted, then method 1500 advances to step 1516. This may correspond to an event where the blockage is not cleared by the pressure from pressure source 1210.

Still further, control module 1200 may monitor the differential pressure between the proximal portion 1410 and the distal portion 1420 of the fluid pathway. If the differential pressure falls below a predetermined pressure, then it may be determined that the blockage has been cleared, and method 1500 advances to step 1516.

In step 1516, the vent valve is closed. In an exemplary embodiment, control module 1200 closes valve 1220.

In step 1518, the pressure source is decoupled from the fluid pathway. In an exemplary embodiment, control module 1200 decouples pressure source 1210 from the distal portion 1420 of fluid pathway 1400.

While the above steps are described in an exemplary order, it will be understood that the above-described method is not so limited. For example, step 1512 may be performed before, after, or simultaneously with step 1510. Similarly, step 1518 may be performed before, after, or simultaneously with step 1516.

The fluid pathway clearing and blockage detection/removal made possible according to aspects of this invention provide substantial benefits. Specifically, there are benefits in terms of at least one of system operation, clinical outcomes, and health care cost management.

Regarding operational benefits, the system is optionally configured to operate automatically to identify and substantially remove tube blockages that may occur in the drainage line or fluid pathway. Also, the system allows the suction device to keep the fluid pathway more clear during operation by optimizing fluid evacuation. Additionally, it provides the ability to apply differential pressure that is not only adaptable for each patient, but also for different times for each patient according to changes in properties of the fluids removed. Finally, the system detects when the collection device is full and/or blocked. Other operational benefits will be appreciated by those having skill in this art.

Regarding clinical benefits, the system can help to maximize the ability for a patient to expel air, providing an overall improved patient outcome. It can also help clear any blockage or partial or complete obstruction in the fluid pathway in a shorter duration and reduced magnitude of applied pressure on a patient as compared with other systems including the manual raising of a blocked tube. Other clinical benefits will be appreciated by those having skill in this art.

Regarding cost benefits, the system makes it possible to benefit from decreased cost per treatment of a patient, as well as reduced costs of the hospital, insurance company and medical system in general. It can also help achieve a reduced length of patient stay in the hospital as clinical outcomes are improved. Other cost benefits will be appreciated by those having skill in this art.

In accordance with other aspects of the present invention, it is desirable that the collection device be separable from the control module and operates as a gravity-based drain without interrupting the patient connections. The system may detect whether or not the collection device is loaded in the control module (e.g., when a user changes a full canister or uses it temporarily as a gravity-based drain). One can optionally use gravity whether the canister is in connection with the system or not (e.g., by shutting off wall suction or battery power). Also, the system can be configured to apply some suction without having battery power.

The system is desirably able to account for when the canister is disconnected and report that condition to the user of the system. The system can detect whether or not a canister is loaded in the system when a user changes the canister. The system has a means such as a tube clamp to prevent air from entering the patient when the canister is disconnected after use. The user can disconnect the tube set from the canister, while the canister is loaded in the control module. When a collection device is not loaded and wall suction is detected, the control module may desirably close all possible pneumatic paths in order to prevent unfiltered air from passing through the control module.

Referring to the drawings, FIGS. 5A-5D illustrate another exemplary chest drainage system 2100 in accordance with aspects of the present invention. System 2100 is usable to drain fluid from the pleural cavity of a patient. As a general overview, system 2100 includes a control module 2200, a collection device 2300, and a fluid pathway defined by a tube set 2400. Additional details of chest drainage system 2100 will be provided herein.

Control module 2200 houses the electronic components of system 2100. Control module 2200 may include any or all of the features described above with respect to control modules 200 and 1200.

Control module 2200 also includes a reusable body portion 2202 that includes ports 2204, 2205, and 2207, among other features. Port 2204 is a vent port configured to releasably couple to a corresponding port 2305 on collection device 2300, suction port 2205 is provided for coupling to a source of suction such as wall suction, and suction port 2207 is provided for coupling to a corresponding port 2306 on collection device 2300. Control module 2200 may desirably include a sensor configured to detect whether the collection device 2300 is connected. In an exemplary embodiment, the sensor is a mechanical switch that is actuated when collection device 2300 is connected.

Figure 5A:
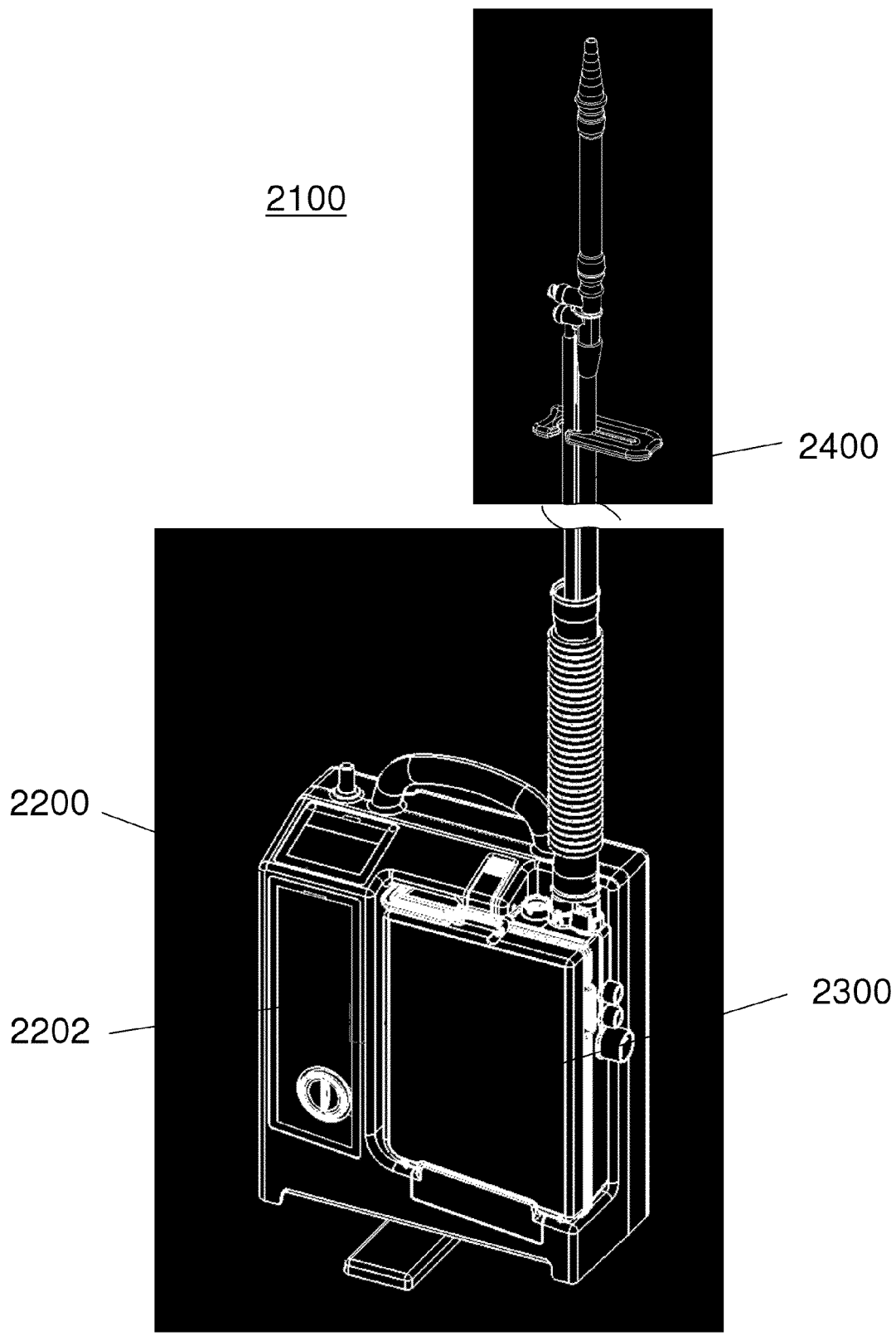
FIGS. 5A-5D are images illustrating another exemplary chest drainage system in accordance with aspects of the present invention.
Figure 5B:
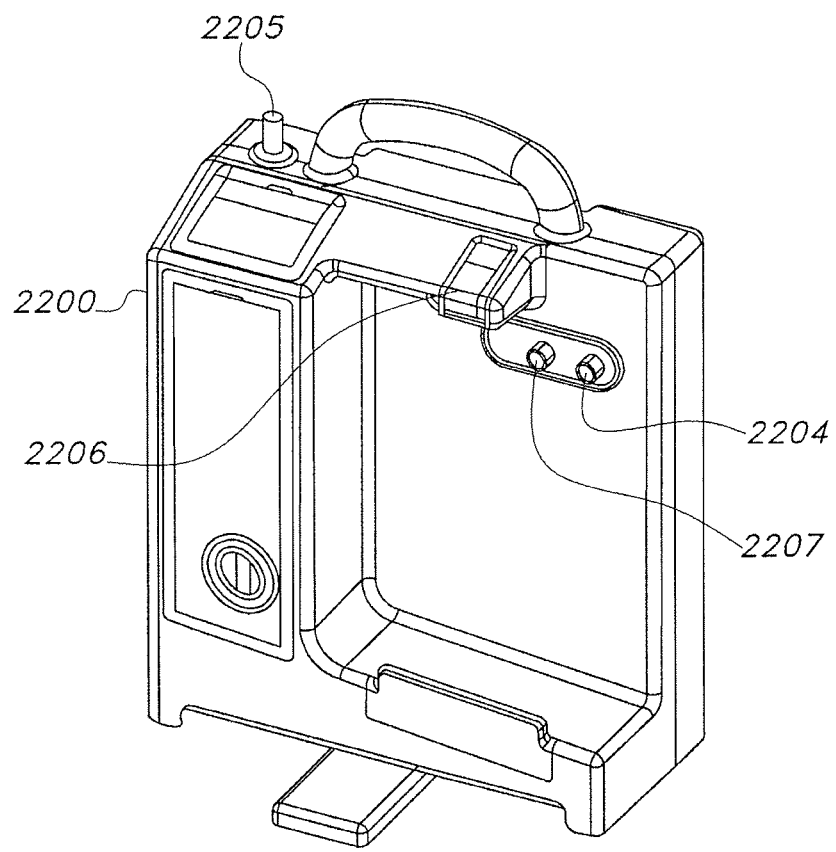
Figure 5C:
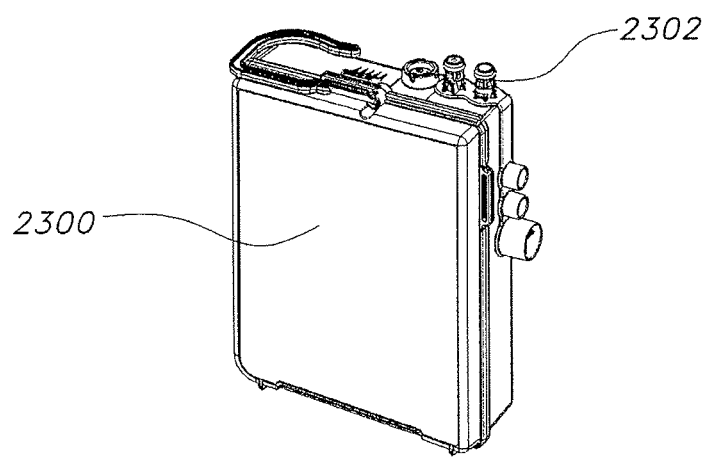

As is most clearly shown in FIG. 5B, the control module 2200 includes a latch 2206 that releasably retains the collection device 2300 within a recess defined by the body of the reusable body portion 2202 of the control module 2200. The latch mechanism 2206 is a mechanical coupling device that engages the collection device 2300 when it is placed in the recess of the control module 2200. Upon pressing or otherwise moving the latch mechanism 2206, it releases the collection device 2300 for replacement, for ambulation, or for access to collected fluids, for example.

In the illustrated embodiment, the latch 2206 is shown at the top center of the control module 2200 for engaging a surface on the top portion of the collection device. It will be appreciated that the latch 2206 may be positioned elsewhere or that various forms of mechanical or electrical or magnetic latch mechanisms are alternatively used.

As described previously, ports of the control module 2200 will mate with ports of the collection device 2300 when the collection device 2300 is latched to the control module 2200. Accordingly, the drainage system preferably includes surfaces or components positioned to promote alignment of those ports as they are connected.

Collection device 2300 collects fluid drained from the patient. Collection device 2300 may include any or all of the features described above with respect to collection device 300 or 1300. In an exemplary embodiment, collection device 2300 is a removable and/or replaceable collection canister that is removably connectable with control module 2200. Collection device 2300 includes at least one inlet port 2302 and at least one outlet port 2306. The output port 2306 of collection device 2300 is configured to be connected with inlet port 2207 of control module 2200 in order to receive suction pressure from control module 2200. Therefore, a suction path is formed that extends from a suction source such as wall suction, through port 2205, through port 2207, through port 2306, through port 2302, and into the drainage lumen of the tube set 2400. Also, a vent path or line is formed that extends from the vent port 2204, through the vent port 2305, via a conduit to the vent port 2303, and into a vent lumen of the tube set 2400.

Fluid pathway of tube set 2400 provides a path for fluid from the patient to drain into collection device 2300. Fluid pathway 2400 is configured to connect to inlet port 2302 of collection device 2300, and extend from collection device 2300 to the patient. Fluid pathway 2400 may include any or all of the features described above with respect to fluid pathways 400 or 1400.

Figure 5D:
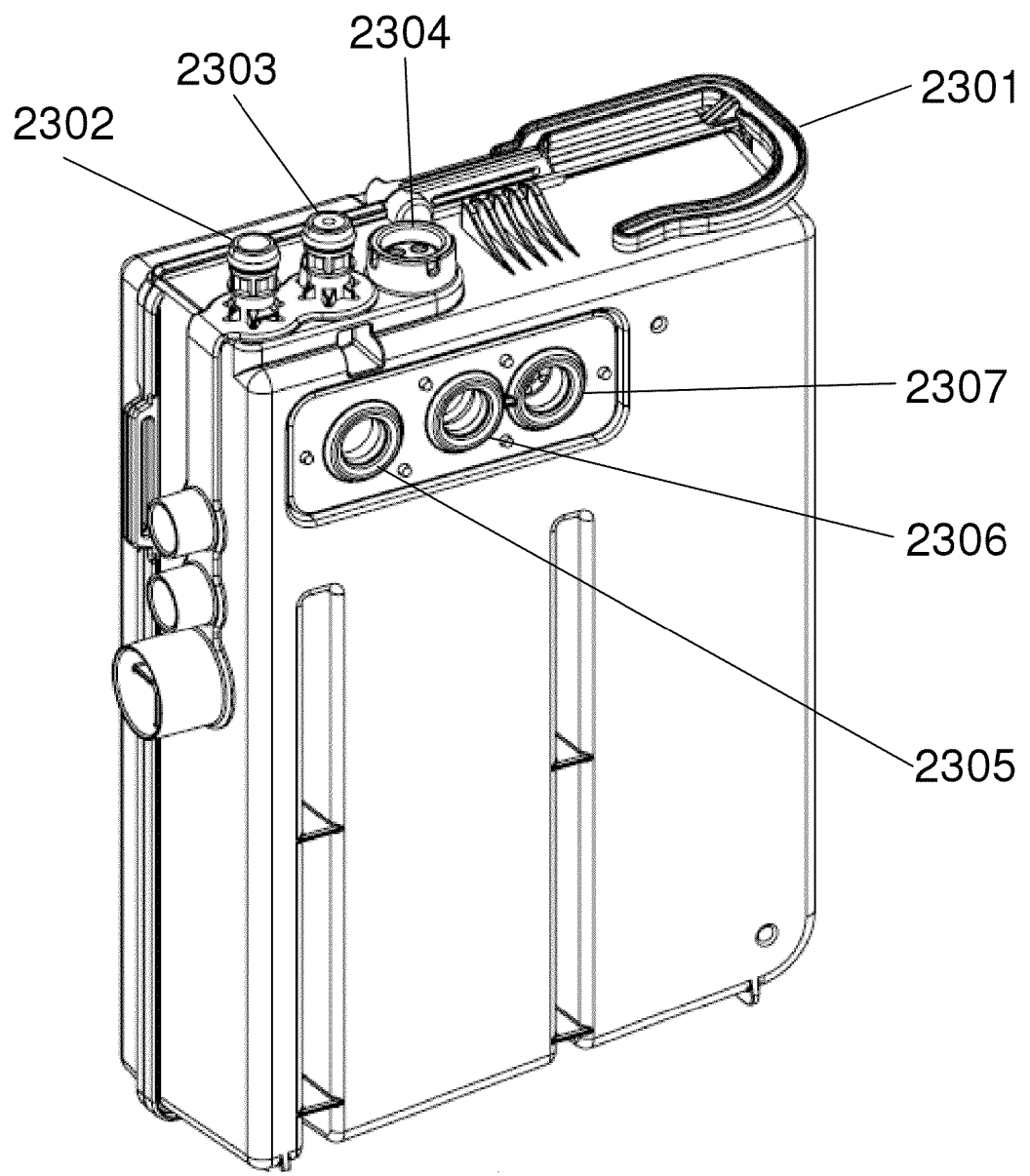

When coupled, ports of the collection device 2300 are coupled for fluid flow with ports of the control module 2200. Specifically, vent port 2204 of control module 2200 is coupled to vent port 2305 of the collection device 2300, and suction port 2207 of control module 2200 is coupled to vent port 2306 of the collection device 2300. Collection device 2300 also includes a relief port 2307 for relief of positive pressure within the device. Accordingly, as best illustrated in FIG. 5D, the port 2305 on collection device 2300 is for a vent line, port 2306 is a suction port, and port 2307 is a relief valve such as a vacuum protection valve.

Specifically, port 2307 allows patient low pressure venting at a relatively low threshold (e.g., +2 cm $H_2O$) for primary, use when the canister is disconnected from the control module 2200. When connected, however, the control module 2200 modulates and controls the venting at such a threshold (e.g., +2 cm $H_2O$). However, port 2304 on the top of the collection device 2300 is a relief valve such as a vacuum protection valve that is set as a higher threshold (e.g., +10 cm $H_2O$), which provides additional protection to the patient should, for example, the power to the system be lost.

This feature is beneficial because it helps to protect the patient when disconnecting the collection device 2300. Also, the collection device 2300 is thus provided with two check valves at different cracking pressures. When the collection chamber 2300 is loaded into the control module 2200, the check valve port 2307 on the back of the collection device 2300 is blocked with a cap or plug (see item 1264 in FIG. 2 for example). This allows the air pressures that are <10 cm $H_2O$ to be monitored and measured by the control module 2200, which is itself able to vent off electronically pressures that are below +10 cm $H_2O$ at any programmed setting (e.g., +2 cm $H_2O$). When the collection device 2300 is not loaded in the control module 2200, however, the check valve port 2307 is no longer blocked; thereby, maximizing performance of the system by allowing air to escape at relatively low cracking pressures.

Collection device 2300 is operable to collect fluid via the fluid pathway 2400 using (i) gravity to draw the fluid through fluid pathway 2400 when disconnected from control module 2200 or (ii) suction pressure when connected with control module 2200. When collection device 2300 is uncoupled from control module 2200, collection device 2300 is configured to automatically close and seal its outlet port. This may be desirable to prevent air leakage from the pleural cavity of the patient. Collection device 2300 may be alternated between gravity- and suction-based fluid collection without interrupting a fluid connection between the patient and the collection device 2300 via the fluid pathway 2400. Switching the device between gravity- and suction-based fluid collection may be performed by connecting or disconnecting collection device 2300 from control module 2200. In other words, when the removable and/or replaceable component is connected, suction can be applied or not (i.e., suction or gravity operation), but when it is disconnected there is no suction applied. The act of disconnecting the removable and/or replaceable canister can therefore remove suction if it is being applied but would not change from gravity mode when disconnected. In this way, leakage to the patient is avoided.

Additionally, collection device 2300 includes a hanger 2301 coupled to a top surface. Hanger 2301 can be pivoted from a stored position, for when the device 2300 is stowed in the module 2200, into an extended position when the device 2300 is separated from the module 2200 for hanging the device 2300 from a structure such as a hospital bed rail.

The removable and/or replaceable canister system made possible according to aspects of this invention provide substantial benefits. Specifically, there are benefits in terms of at least one of system operation, clinical outcomes, and health care cost management. For example, it helps to provide meaningful information to health care professionals when it is configured to detect and indicate when the patient is and is not connected to the system. It can also be more sanitary in instances with diseased patients (e.g., the ability to have the canister automatically close when removed), thus providing a clinical benefit. Finally, it provides an economical solution in that a portion of the system is reusable. Generally, there is a significant benefit of permitting the canister to alternate between gravity and suction instead of just either one or the other. Other benefits will be appreciated by those having skill in this art.

In accordance with aspects of the present invention, a chest drainage system may desirably measure and inform the user of patient air leaks. The system may monitor an air leak over time without measuring volumetric flow rate; instead, it may desirably record the time that a patient has any air leak (e.g., 0 $cmH_2O$ or +2 $cmH_2O$) during predetermined time increments. The system is able to account for when the collection device is disconnected and report that condition to the user of the system. It can optionally report an empty "x" 15 min increment column or alternatively show some of it. For example, if the canister is attached 14 out of 15 minutes of an increment, data may be shown. Alternatively, if there is a single second of disconnect in any increment, that entire increment can be reported as a disconnect.

The system desirably includes a display for showing the last recorded air leak trend increment in terms of % of time that the patient has any air leak. The system optionally records the time and/or reports out to the user the occurrence of an air leak over time. For example, it can report how many times it flashed Red/"Total Flashes" in a time increment such as 15 min., provide an integral of the waveform for pressure indications over +2 cm $H_2O$, provide the counted time pressure is over +2, and other indications. The system can therefore record and/or display any inability of a patient to maintain sub-atmospheric pressure, due to a leak in the patient's pleural cavity.

In an exemplary embodiment, the system is configured to measure a variation in the pressure waveform generated by the patient. This is achieved by determining inflection points on the waveform curve. Preferably, the trending display can disregard events such as the actuation of the clearing function. The system displays the air leak trending history (e.g., over the last 12 hours) in increments (e.g., 15 minute increments) and includes an indication when the canister has been disconnected.

The system displays the last recorded air leak trend increment in terms of % from 0% to 100%. The system can display the air leak trending history of the last 12 hours in 15 minutes increments and it may include when the canister has been disconnected. The air leak trend history may be cleared upon power cycling.

When the control module detects an air leak under gravity (e.g., =>+2.0 $cmH_2O$), it may desirably provide a RED visual notification to the user. When the control module detects an indeterminate air leak under gravity (e.g., between −1 and +2.0 $cmH_2O$), it may desirably provide a YELLOW visual notification to the user. And when the control module detects no air leak under gravity (e.g., <=−1 $cmH_2O$), it may desirably provide a GREEN visual notification to the user.

In an exemplary embodiment, the control module provides a visual notification to the user when the control module detects a large continuous air leak. For example, when the system detects an air leak under suction (Pressure>Applied Suction Setting Pressure, >equaling less negative), it provides a RED visual notification to the user. When the control module detects an indeterminate air leak under suction (Pressure=<Applied Suction Setting Pressure, <equaling more negative AND>(Applied Suction Pressure)−1 $cmH_2O$), it provides a YELLOW visual notification to the user (e.g., applied suction pressure is −20 $cmH_2O$, and pressure is equal to or less than −20 $cmH_2O$ and more than −21 $cmH_2O$). When the system detects no air leaks under suction (Pressure=< (Applied Suction Setting Pressure)-1 $cmH_2O$), it provides a GREEN visual notification to the user (e.g., applied suction pressure is −20 $cmH_2O$, and pressure is maintained at equal to or less than −21 $cmH_2O$).

The control module desirably displays the fluctuations of pressure ranges in real-time. When activated, the system preferably shows a display for a predetermined time interval, e.g., 60 seconds. The system may desirably include a service accessible port to enable the user to export pressure waveform data real-time for data acquisition and recording. The system may allow for remote or wireless data export. Additionally, the system may use this data export for reporting on significant changes in patient condition, such as when no air leak is detected in the pleural cavity.

Figure 6:
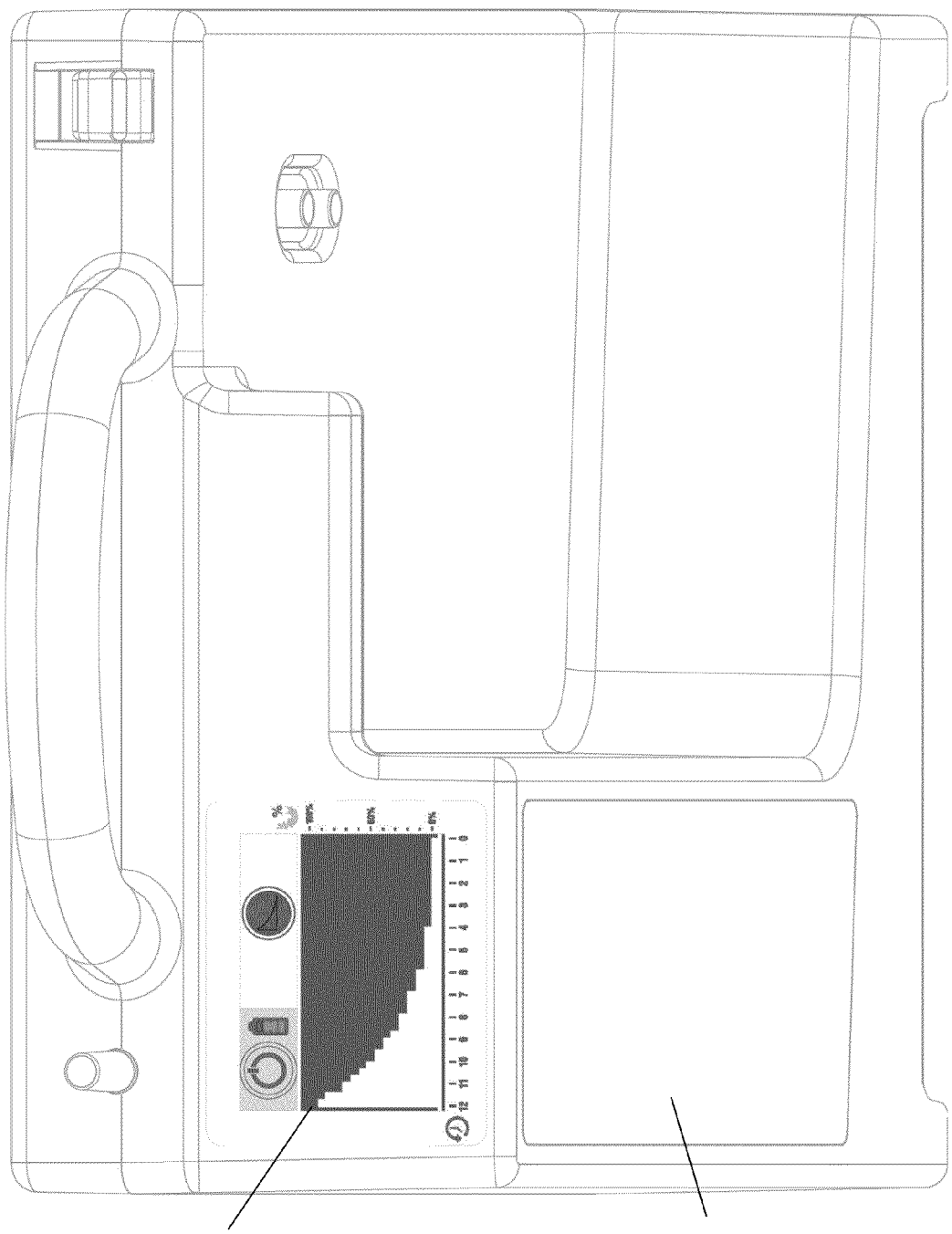
FIG. 6 illustrates another exemplary chest drainage system in accordance with aspects of the present invention.

Referring to the drawings, FIG. 6 illustrates another exemplary chest drainage system 3100 in accordance with aspects of the present invention. System 3100 is usable to drain fluid from the pleural cavity of a patient. As a general overview, system 3100 includes a control module 3200, a collection device (not shown), and a fluid pathway (not shown). Additional details of chest drainage system 3100 will be provided herein.

Control module 3200 houses the electronic components of system 3100. Control module 3200 may include any or all of the features described above with respect to control modules 200, 1200 and 2200. The collection device collects fluid drained from the patient. The collection device may include any or all of the features described above with respect to collection devices 300, 1300, and 2300. The fluid pathway provides a path for fluid from the patient to drain into the collection device. The fluid pathway may include any or all of the features described above with respect to fluid pathways 400, 1400, and 2400.

Control module 3200 also includes means for detecting a pressure of the fluid collected by and stored in the collection device. The pressure-detecting means may be configured to sense the pressure of the collection device when the collection device is connected with control module 3200. In an exemplary embodiment, the pressure-detecting means is a pressure sensor. Suitable pressure sensors will be known to one of ordinary skill in the art from the description herein. Other equivalent means will be known to those of skill in this field.

Control module 3200 also includes a display 3202. Display 3202 may be usable to provide a user of system 3100 with any one of a plurality of visual notifications. Desirably, display 3202 is configured to display changes in the pressure of the fluid in the collection device. Display 3202 may display pressure changes in predetermined increments of time, e.g., fifteen minute intervals.

In an exemplary embodiment, display 3202 may be configured to indicate whether and when the collection device is disconnected from control module 3200 during the predetermined time increments. Additionally, display 3202 may be configured to indicate a number of occurrences in which the detected fluid pressure exceeds a predetermined minimum magnitude in each of the predetermined time increments.

Control module 3200 may be programmed to measure a total amount of air leakage based on the pressure measurements of the pressure-detecting means. In this embodiment, display 3202 may be configured to indicate a total amount of air leakage in a respiratory wave form of the patient, or a duration of an air leak having at least a predetermined minimum magnitude. It may also include a display for indicating collected fluid volumes.

Figure 7:
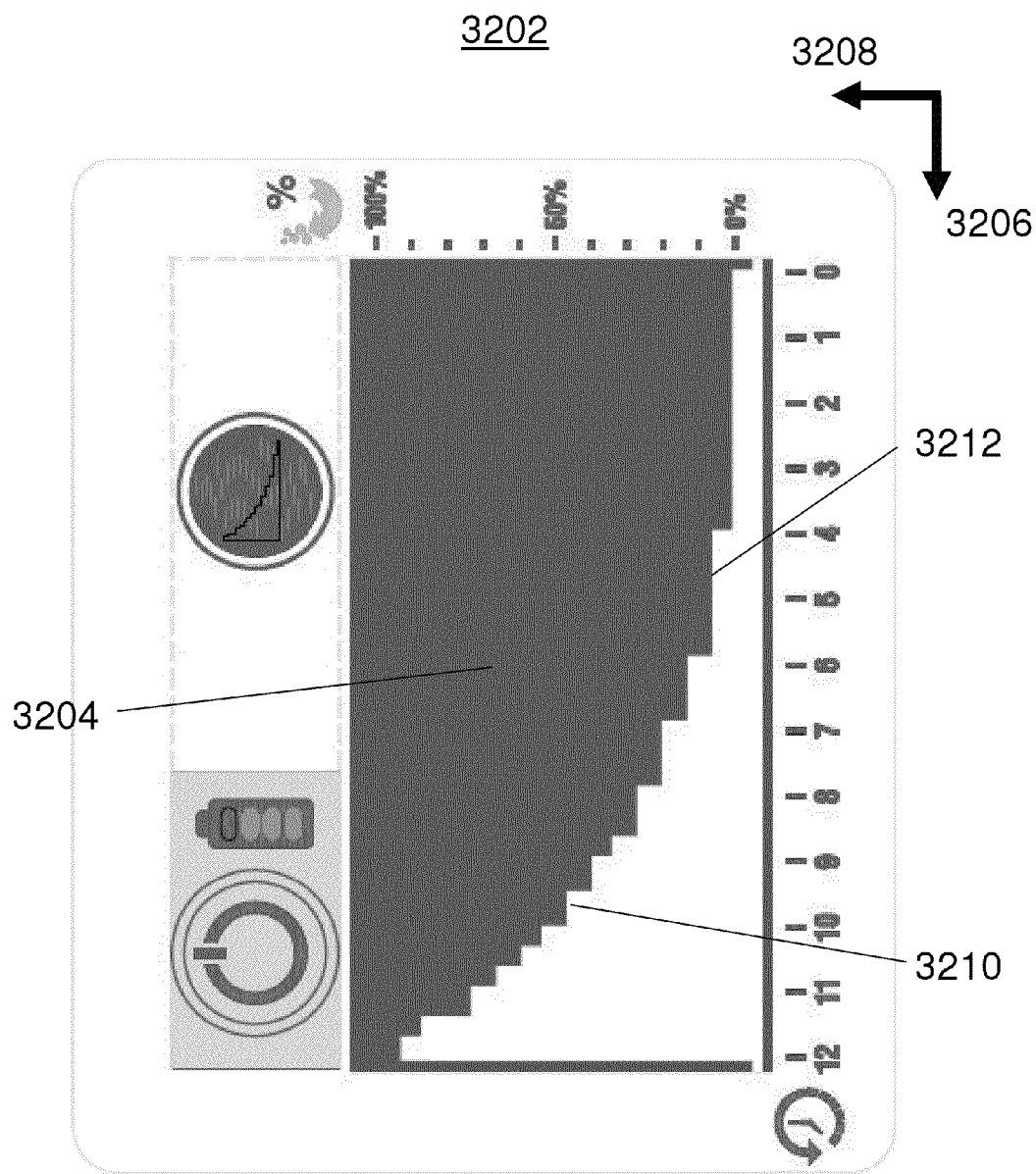
FIG. 7 is an image illustrating an exemplary display of the chest drainage system of FIG. 6.

FIG. 7 illustrates an exemplary display 3202 in accordance with aspects of the present invention. As shown in FIG. 7, display 3202 includes a graph 3204 for presenting information about a patient air leak to a user. As explained below, graph 3204 may display a trend in occurrences of changes in pressure of the fluid collected by collection device 3300 over time. This trend may desirably be based on detections of changes in fluid pressure during predetermined time increments.

The horizontal axis 3206 of graph 3204 represents the time during which the patient air leak has been monitored by system 3100. Desirably, the time may be broken up into predetermined time increments, e.g., 15 minute increments. Accordingly, information may be presented to the user about the patient air leak in 15 minute increments.

The vertical axis 3208 of graph 3204 represents the percentage of time during which the patient experiences an air leak. An air leak in this embodiment may be defined as a predetermined positive pressure, for example, +2 cmH$_2$O. For example, point 3210 on graph 3204 shows a point at which the patient experienced an air leak (e.g., the pressure of the fluid in collection device 3300 was greater than +2 cmH$_2$O) for approximately 50% of the predetermined increment of time (e.g., for 7.5 minutes in a 15 minute increment of time). Conversely, at point 3212 on graph 3204, the patient experienced an air leak for only approximately 10% of the predetermined increment of time (e.g., for 1.5 minutes in a 15 minute increment of time).

More specifically, and according to one exemplary embodiment of the invention, the trending display illustrated in FIG. 7 provides useful information to a clinician or medical practitioner about the status of a particular patient. Specifically, it indicates an approximate percentage of the time, in sequential time increments, during which the patient is experiencing an air leak in his or her pleural cavity. This information is derived from the number of respiratory cycles of the patient during each time increment with and without associated air leaks. This is accomplished, for example, by calculating the ratio of the quantity of respiratory cycles (QRC) of the patient in which there is a detected leak in the time increment (QRC$_{leak}$) to the total quantity of respiratory cycles of the patient in that time increment (QRC$_{total}$). Accordingly, the percentage reported in the trending display is (QRC$_{leak}$/QRC$_{total}$) (100). For example, QRC$_{leak}$=50 if the quantity of respiratory cycles of the patient in which there is a detected leak is 50 in the subject time increment, QRC$_{total}$=100 if the total quantity of respiratory cycles of the patient is 100 in that time increment, and the ratio QRC$_{leak}$/QRC$_{total}$ is 50%. The value 50% would be displayed for the subject time increment, indicating to a clinician that the patient experienced an air leak for about 50% of the time during that time increment.

The preferred display of percentage is beneficial for several reasons. Although the number of air leaks per unit time is optionally displayed as an alternative to percentage, the preferred display of percentage is believed to be more significant from the clinical perspective because it indicates the trend of the prevalence of the air leak over time. Additionally, although the magnitude of air leaks is optionally displayed as an alternative, the preferred display of percentage is clinically important because it relates to the presence or absence of an air leak over a predetermined magnitude (e.g., +2 cmH$_2$O) and the trend in that presence/absence.

It will be understood to one of ordinary skill in the art that the exemplary display 3202 shown in FIG. 7 is shown solely for the purposes of illustration, and is not limiting. Other displays may be incorporated for presenting information to the user on a patient air leak, as would be understood to one of ordinary skill in the art.

According to one exemplary embodiment, a means is provided for detecting a pressure differential in the fluid. The means for detecting a pressure differential in the fluid may include a pressure differential sensor. Although the pressure differential detecting means could optionally include a bubble detection chamber, the means for detecting a pressure differential according to exemplary embodiments eliminates the need for bubble detection such as that provided by the bubble detection chamber disclosed in U.S. Pat. No. 7,207,946. This is beneficial in that it enables the use of a "dry" system and can eliminate inconveniences and cost associated with a liquid-filled component that generates bubbles.

According to one exemplary embodiment of the invention, a display is provided to display a trend in occurrences of changes in pressure of the fluid over time in predetermined time increments based on a number of detections of pressure differentials that exceed a predetermined pressure differential during each of the predetermined time increments, the trend being correlative to the percentage of time that the patient is deemed to have an air leak in the pleural cavity in the predetermined time increments. For example, the system is optionally configured to detect pressure differentials that may occur in each breath cycle of a patient. Such pressure differential may or may not reach a predetermined minimum value (e.g., +2 cm H$_2$O), but may build until it does exceed that predetermined minimum value. When that value is exceeded, the system is optionally configured to count how many times the value is exceeded in a particular time interval. This number of times is reported in the display and is considered correlative to the percentage of time that a patient is deemed to have an air leak in the pleural cavity in the time increments.

The trend display feature made possible according to aspects of this invention provides substantial benefits. Specifically, there are benefits in terms of at least one of system operation, clinical outcomes, and health care cost management. For example, when using this feature, a clinician can make more informed patient assessments based on the trending data (such as the trending data illustrated in FIG. 7). It also provides an objective indication of the air leak of the patient over time, by providing a predictable, reproducible, explainable, and translatable system. More specifically, it makes it possible to indicate the percentage of the time a patient has an air leak, which may be advantageous as compared to alternatively providing an indication based on a magnitude or quantity of fluid being leaked. Additionally, the fluid pathway clearing aspect of the system and the trending display function can operate together as an integrated system. Other benefits will be appreciated by those having skill in this art.

Figure 8:
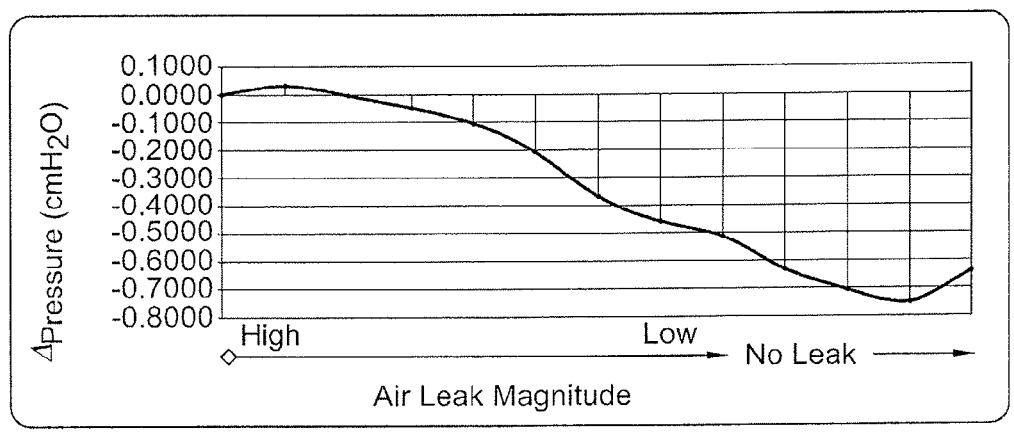
FIG. 8 is a graph illustrating measurements of the decay in pressure in the pleural cavity of a patient as a function of time in accordance with an aspect of the present invention.

FIG. 8 is a graph depicting the pressure within the pleural space of a patient in accordance with an aspect of the present invention. The disclosed chest drainage system may be configured and used to measure the pressure within the pleural space without restricting the flow in the drainage catheter. The rate of decay of the pressure in the pleural cavity correlates to the assessment of a patient air leak in the pleural cavity. Accordingly, the disclosed chest drainage system may be used to monitor an air leak in a pleural cavity of a patient. Monitoring the air leak of the patient's pleural cavity can provide valuable information regarding treatment and recovery of the patient. This information may include providing the medical staff with increased knowledge and understanding on how a post-operative air leak is healing during patient recovery. This may further lead to establishing reliable data for pattern recognition for multiple patients to assist a doctor or medical practitioner in the consideration of when to remove a chest tube. This information in turn may potentially shorten the length of hospital stay a patient may require following thoracic surgery.

Air leaks within the pleural cavity are monitored by measuring the rate of pressure decay in the pleural cavity of a patient, correlating the rate of pressure decay to an associated air leak, and generating an indicator showing a trend in the magnitude of the air leak in the pleural cavity. As described above, the rate of exerted pressure decay in the pleural cavity of a patient may be measured using the disclosed chest drainage system.

It has been discovered that the relationship of the trend in air leak resolution is proportional to the measured pressure decay and can be expressed by the following relationship:

$$Q_{Airleak} \propto \int Pdt$$

where:
$Q_{Airleak}$ is an extrapolated air leak,
P is a measured pressure, and
t is time.

Accordingly, the patient air leak correlates to the rate of pressure decay in the pleural space of the patient.

Figure 9:
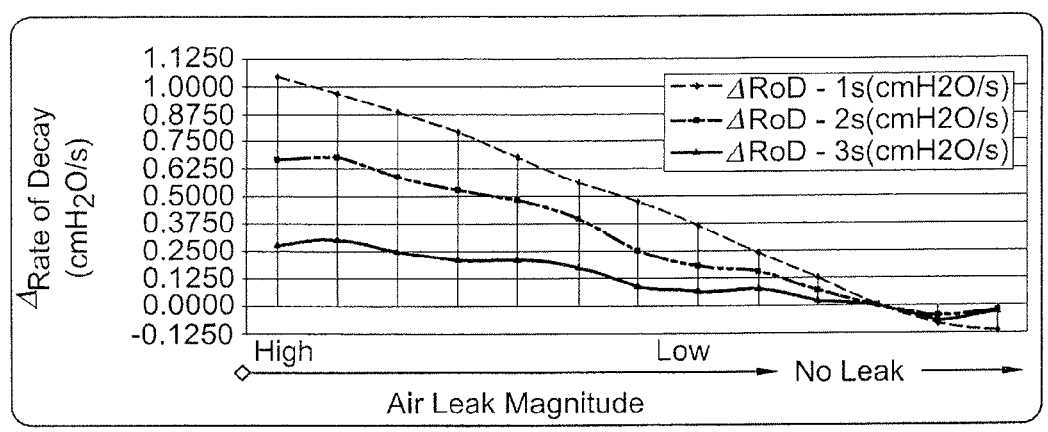
FIG. 9 is a graph illustrating the trend and rates of pressure decay relating to an associated patient air leak as a function of time in accordance with an aspect of the present invention.

FIG. 9 is a graph depicting the rate of pressure decay within the pleural space of a patient in accordance with an aspect of the present invention. Using the above correlation, the chest drainage system is able to quantify the trend and rate of decay as a function of air leak over differing time intervals. Changes and resolution of the patient air leak as a function of clinical healing are detected by a reduction in the measured pressure decay rate, and can then be correlated to a reduced air leak by the above algorithm.

An indicator can be generated depending on the variation in patient air leak. For example, the change in pressure decay and proportional correlation to air leak variation can be accumulated and the feedback presented by a varying trend analysis. The generated indicator may include a simple light means where a reduction in air leak over a determined period of time correlates to a change in the emitted light. According to one exemplary embodiment, this includes a progressive Red to Yellow to Green light indication. In this embodiment, the progressive change in the light color provides the clinician with information related to the reduction in the air leak and improvement of the overall pleural health of the patient.

As described previously in connection with FIGS. 6 and 7, the system measures the pressures in the system and detects when the pressures reach a positive pressure of a predetermined magnitude (e.g., 2 cmH$_2$O). Every time the pressure exceeds this threshold in one embodiment, the system records the data and is able to report this out in a trend chart as (Times pressure exceeded Threshold/Time) where time, for example, could be reported in increments such as 15 minute increments.

Another method of quantifying the air leak could include taking recorded pressure waveforms and measuring the area under the pressure waveform that is above a predetermined threshold. The quantification of air leak relative to time as a means to provide an objective assessment for patients is beneficial. Many methods could be used to do so, including counting the number of times pressure exceeds a pressure threshold, measuring the duration of time pressure exceeds a pressure threshold, determining an area of a pressure waveform that is above a pressure threshold, determining the average of the maximum pressures at the times when the pressure exceeds a pressure threshold, for example. Such quantification in a clinical setting provides an objective assessment of the leak integrity of the patient as a measure of patient healing progression. Having this objective data would, for example, help clinicians to make decisions that are based on standardized means of measuring air leaks.

When suction is applied, the quantification of air can be captured by several means. First, if an air leak is large enough, then under suction, the system would be able to measure a difference between the intended applied suction and the measured pressure in the collection device or canister. If the measured pressure in the canister is less negative than the intended applied suction, then there is presumably an air leak in the patient (assuming that the system is not a collapsible system and that there are no defects in the system).

If the air leak is small, then the system can apply the suction and then temporarily shut off the source of the suction and seal the negative charged system (canister, tube set, and pleural space). The system can then monitor the pressure and look for pressure decay. The system can report the trend of an air leak and can do so with several methods.

One such method would be to note the times when the system has a measured difference or a pressure decay under suction and then translate this to a percentage of time in this state over time (e.g., where time could be in increments such as 15 min increments). Alternatively, objective quantification of the air leak can be performed by measuring the area of the pressure differential curve over time in combination with the area of the curve of the rate of decay. Since it is preferred to report data as a single data set (e.g., percentage of air leaks over time, versus percentage of air leaks under gravity over time and percentage of air leaks under suction), a calibrating constant may be factored in to get optimized percentage air leak trend reporting.

The decay algorithm feature made possible according to aspects of this invention provides substantial benefits. For example, for a given unit of time, it may be more preferred to measure pressure decay than to measure flow as an indicator of an air leak. Also, it provides an objective view of the air leak of the patient over time. As an optional alternative to measuring flow per unit of time, the decay algorithm and the indicator allow a clinician to tell over a unit of time if a leak is steady, improving, or getting worse. Other benefits will be appreciated by those having skill in this art.

Figure 10:
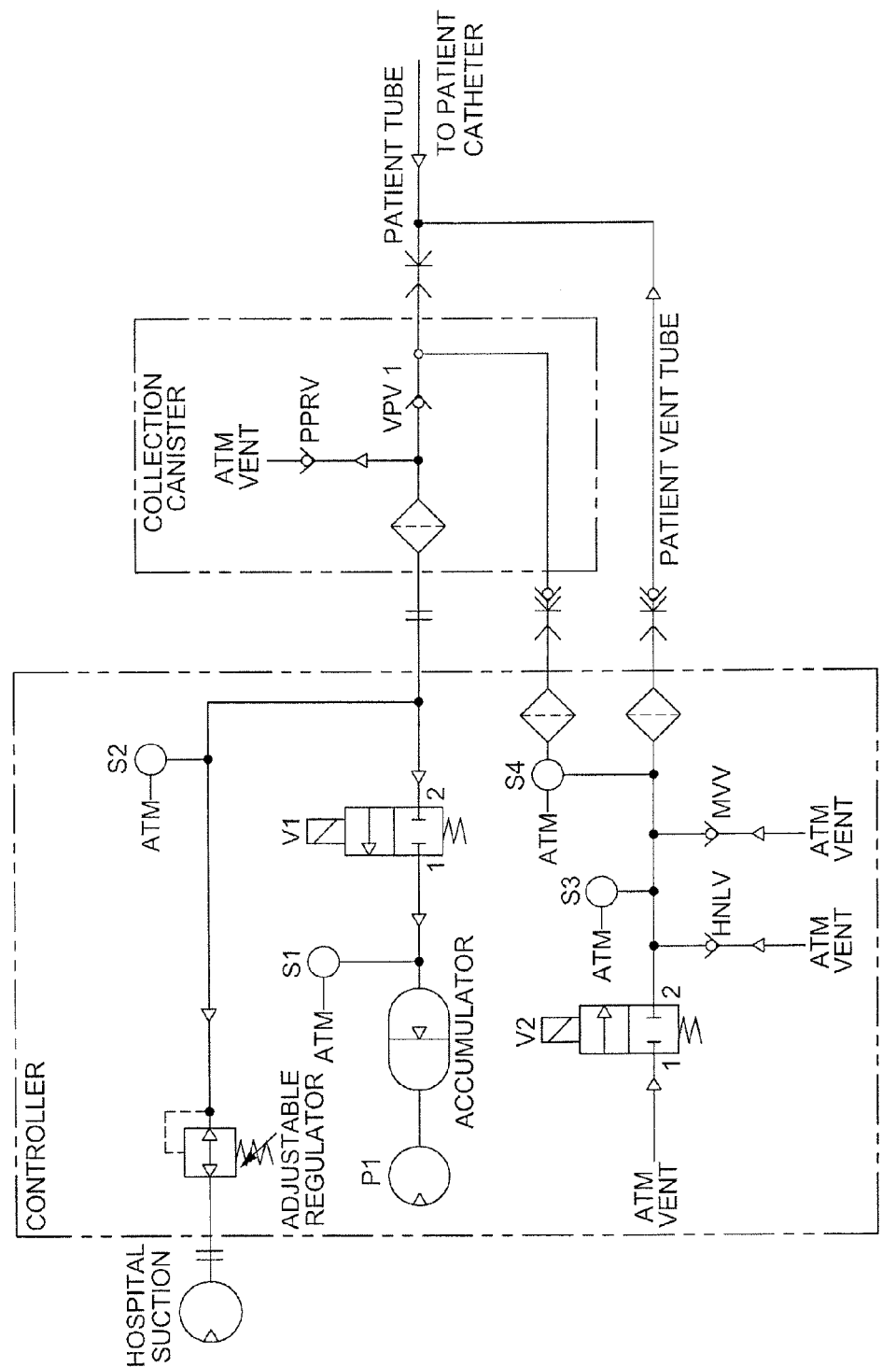
FIG. 10 is a schematic diagram illustrating an exemplary arrangement of electrical components that can be used in a chest drainage system in accordance with aspects of the present invention.

Another exemplary embodiment, in which a chest drainage system includes a fluid clearing device, is illustrated schematically in FIG. 10. The fluid clearing device removes fluid or blockages from within a patient tube automatically when a predefined pressure differential exists between the measured pressure at the patient (from pressure sensor S3) and the measured pressure within the fluid collector (from pressure sensor S4). Alternatively the fluid clearing device can be activated based on a fixed or selectable timer.

The fluid-clearing device includes an accumulator and a vacuum pump P1, as illustrated schematically in FIG. 10. When the fluid-clearing device is activated, the accumulator will have its air volume drawn down to −600 cmH$_2$O negative vacuum pressure using vacuum pump P1. A vacuum sensor S1 inline with the fluid collector may be used to determine the pressure of the accumulator and shut off the pump P1 when the accumulator reaches the desired negative pressure. The fluid-clearing device may also include a microcontroller for controlling the activation of the accumulator.

The accumulator may be closed off by a magnetic valve V1 in order to store the energy (−600 cmH$_2$O) within the accumulator until the magnetic valve is signaled to activate. Valve V1 may be activated when the differential pressure measured between pressure sensor S3 and pressure sensor S4 reaches a predefined differential pressure, at which time the stored energy will be released from the accumulator while simultaneously opening a separate vent valve V2 to allow the fluid within the patient tube to flow into the fluid collector. Opening vent valve V2 may allow differential pressure to enter at the patient tube, thereby preventing exposure of the patient to high negative pressure. The stored negative pressure from the accumulator will draw the fluid away from the patient and into the fluid collector. Alternatively, the accumulator stored pressure may be adjusted by the algorithm described above, and set point values other than −600 cmH$_2$O may be utilized as determined to be most clinically relevant. Additionally, the accumulator stored pressure may be adjusted based on desired power usable by pump P1 and necessary negative pressure for removing a blockage.

It may be desirable to clear the patient tube in order to assure accurate volumetric measurement of the collected fluid by preventing fluid collected within the tube from not being recorded, which may create variability in the clinical assessment of the collected drainage. It may also provide clinical benefit by keeping the tube clear so as to facilitate further drainage and to minimize the backpressure created to a patient trying to expel an air leak. This feature may also minimize care and effort for the clinical staff.

Vacuum pump P1 may desirably be a diaphragm vacuum pump. The accumulator may desirably be a 300 cc volumetric vessel accumulator for example. Other volumetric vessel capacities are optionally utilized.

Figure 11A:
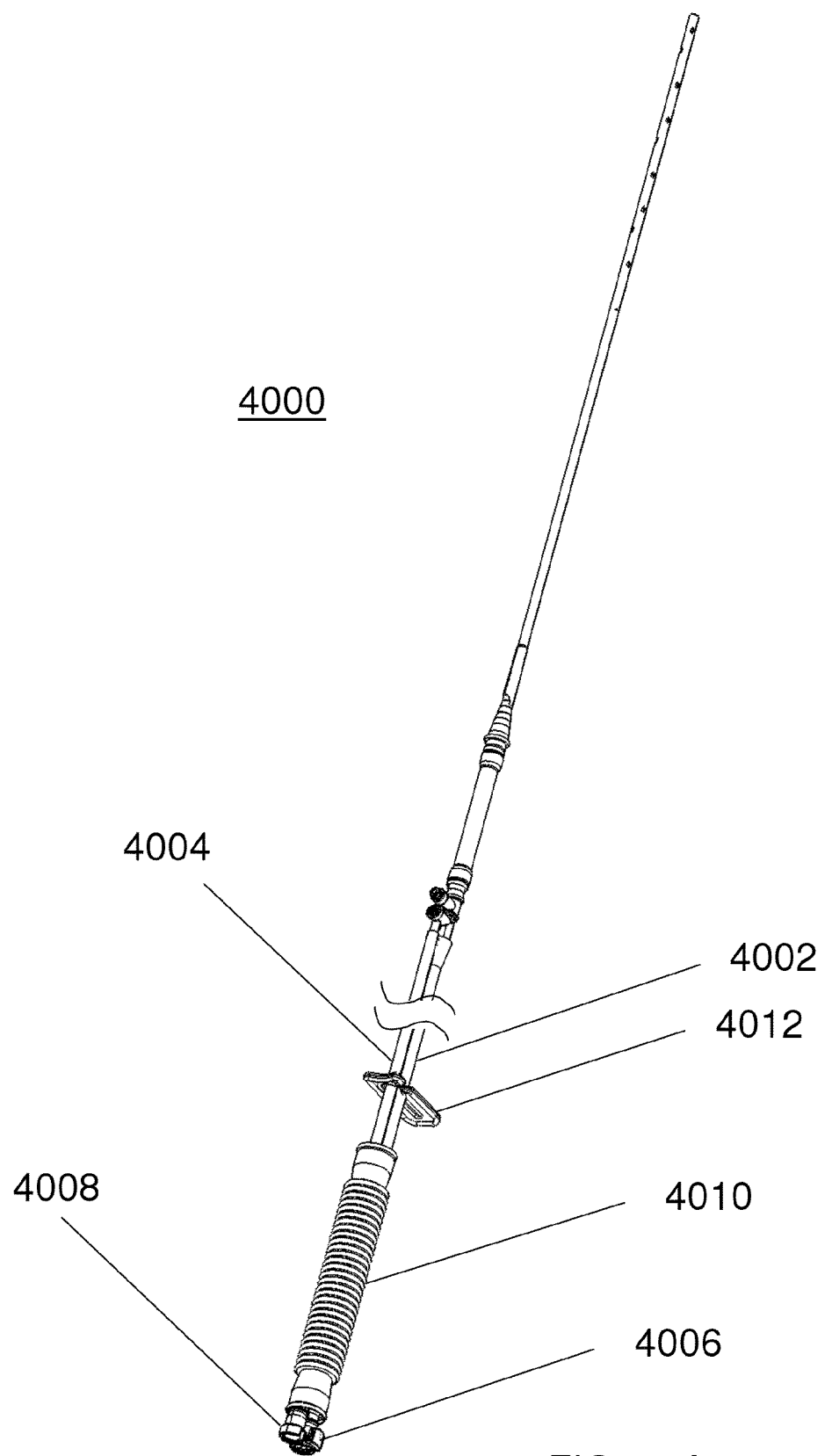
FIGS. 11A and 11B illustrate an exemplary tube set that can be used in a chest drainage system in accordance with aspects of the present invention.
Figure 11B:
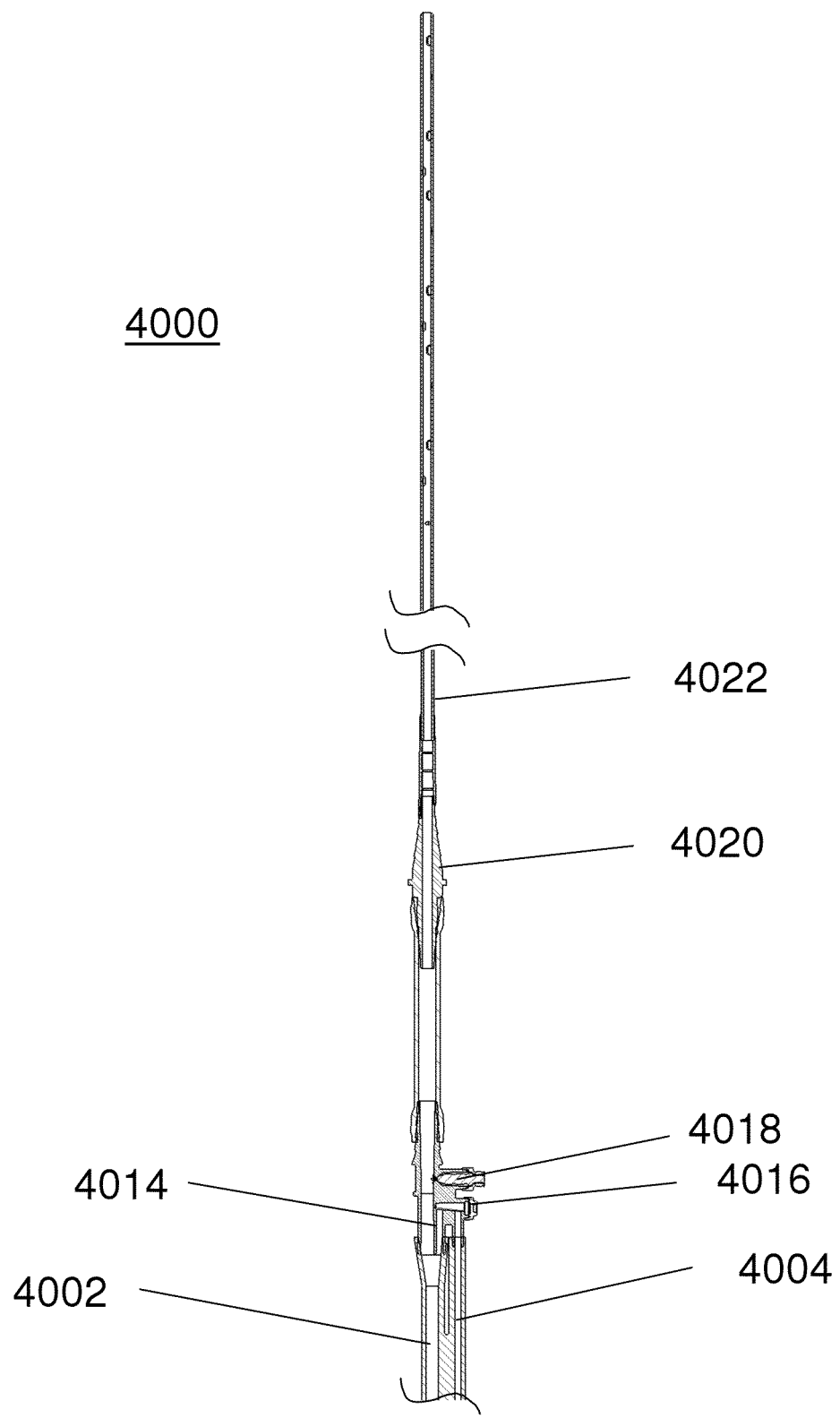

Referring now to FIGS. 11A and 11B, and exemplary tube set 4000 that can be used in the chest drainage system will now be described. Tube set 4000 may include features of tube set 2400 illustrated in FIG. 5B.

As shown in FIGS. 11A and 11B, tube set 4000 includes two lumens 4002 and 4004. The first lumen 4002 provides a conduit for draining fluid from the patient. The first lumen 4002 includes an outlet port 4006. Fluid drained from the patient may pass through first lumen 4002 and out of outlet port 4006 into the collection device via drain port 2302. Second lumen 4004 provides a conduit for releasing pressure in lumen 4002. Second lumen 4004 includes an inlet port 4008 for selectively coupling second lumen 4008 to open air. Inlet port 4008 may be connected to a vent line formed as part of either a collection device or a control module. For example, inlet port 4008 can be connected to port 2303 of the collection device 2300.

Tube set 4000 may further include a stress-relief portion 4010. Stress-relief portion 4010 may be provided adjacent outlet ports 4006 and 4008, as shown in FIG. 11A. Stress-relief portion 4010 may prevent kinking in tube set 4000 when tube set 4000 is connected to a corresponding collection device. In an exemplary embodiment, stress-relief portion 4010 comprises a length of corrugated tubing.

Tube set 4000 may also include a hose clamp 4012. Hose clamp 4012 may be usable to prevent air from entering the patient when tube set 4000 is disconnected from the collection device after use.

As shown in FIG. 11B, tube set 4000 includes a connecting portion 4014 that connects lumen 4002 with lumen 4004. Connecting portion 4014 enables lumen 4004 to selectively release the pressure accumulated in lumen 4002. As shown in FIG. 11B, connecting portion 4014 is desirably extends from lumen 4002 in an upstream direction, to prevent fluid drained from the patient from entering lumen 4004.

Tube set 4000 may also include a sealing element 4016. Sealing element 4016 is generally closed but may optionally enable a user of tube set 4000 to directly couple lumens 4002 and 4004 with atmosphere. In an exemplary embodiment, sealing element 4016 is a cap or plug that may be manually inserted or removed or permanently sealed.

Tube set 4000 may also include a needle-less access port 4018. Needle-less access port 4018 may be usable to access and collect the fluid drained from the patient.

Tube set 4000 may also include a catheter connector 4020. Catheter connector 4020 connects tube set 4000 with a conventional patient drain catheter 4022, which may be inserted in a patient to enable drainage of fluid.

The exemplary chest drainage systems and methods disclosed herein provide advantages, as set forth previously. The chest drainage systems described herein produce superior patient outcomes, improve ease of use and objectivity for the clinical decision making process, and maintain a high level of robustness and reliability.

Also, the systems and methods described herein can help health care professionals to determine one or more of the following: the amount of fluid that is being evacuated from a patient; the rate at which the fluid is being evacuated; the presence of an air leak in the pleural spaces of a patient's lungs; whether and when the patient needs suction; when a drainage tube can be pulled; and whether the pleural spaces are infected or not. Finally, the chest drainage systems described herein are environmentally friendly, affordable, mobile, and easy to use with minimal setup and disposal.

Although the invention is illustrated and described herein with reference to specific embodiments, the invention is not intended to be limited to the details shown. Rather, various modifications may be made in the details within the scope and range of equivalents of the claims and without departing from the invention.

What is claimed:

1. A chest drainage system including:
   a collection device configured to receive a first sub-atmospheric pressure from a first pressure source;
   a fluid pathway configured to extend from the collection device to a patient and receive the first sub-atmospheric pressure via the collection device, the fluid pathway having a proximal portion configured to extend proximally toward the patient and a distal portion configured to extend distally from the patient;
   a second pressure source configured to selectively generate a second sub-atmospheric pressure more negative than the first sub-atmospheric pressure;
   a pressure accumulator configured to store the second sub-atmospheric pressure generated by the second pressure source, the second pressure source and the pressure accumulator coupled to the collection device at a location outside of the fluid pathway; and
   a valve positioned between the collection device and the pressure accumulator and configured to selectively couple the pressure accumulator to the proximal portion of the fluid pathway via the collection device,
   wherein the system has a first state in which the valve is closed and the pressure accumulator is not coupled to the fluid pathway, and a second state in which the valve is opened and the second sub-atmospheric pressure from the pressure accumulator is introduced into the proximal portion of the fluid pathway, the second state occurring when a predetermined pressure differential is detected between the proximal and distal portions of the fluid pathway.

2. The system of claim 1, wherein the pressure source includes means for generating the sub-atmospheric pressure and providing the sub-atmospheric pressure to the pressure accumulator.

3. The system of claim 2, wherein the means for generating the sub-atmospheric pressure comprises a pump.

4. The system of claim 2, wherein the means for generating the sub-atmospheric pressure comprises an external suction source.

5. The system of claim 1, wherein the system substantially maintains a prescribed pressure at the patient when the valve is opened and the sub-atmospheric pressure is introduced.

6. The system of claim 1, wherein the system is configured to be coupled to an external suction source to provide suction to the distal portion of the fluid pathway.

7. A chest drainage system comprising:
- a collection device;
- a fluid pathway configured to extend from the collection device to a patient, the fluid pathway having a proximal portion configured to extend proximally toward the patient and a distal portion configured to extend distally from the patient;
- a pressure source configured to maintain a first sub-atmospheric pressure within the collection device and the fluid pathway;
- a sensor system configured to sense a pressure differential between the proximal and distal portions of the fluid pathway;
- means for substantially clearing a blockage in the fluid pathway between the proximal and distal portions of the fluid pathway, the clearing means comprising a pressure accumulator configured to store a second sub-atmospheric pressure more negative than the first sub-atmospheric pressure, the pressure accumulator selectively coupled to the fluid pathway via the collection device; and
- means for determining when to actuate the clearing means based on at least one of the pressure differential sensed by the sensor system and an elapsed time of operation of the chest drainage system, the determining means recognizing a first state in which the clearing means is not coupled to the fluid pathway, and a second state in which the clearing means is coupled to the fluid pathway and the sub-atmospheric pressure from the clearing means is introduced into the fluid pathway.

8. A fluid pathway clearing apparatus for a chest drainage system including a collection device configured to receive a first sub-atmospheric pressure from a first pressure source and a fluid pathway configured to extend from a patient to the collection device and provide the first sub-atmospheric pressure to the patient via the collection device, the fluid pathway having a proximal portion configured to extend proximally toward the patient and a distal portion configured to extend distally from the patient, the apparatus comprising:
- a second pressure source configured to generate sub-atmospheric pressure;
- a pressure accumulator configured to store the sub-atmospheric pressure generated by the pressure source and to be coupled to the chest drain system for providing the sub-atmospheric pressure to the distal portion of the fluid pathway; and
- a valve configured to couple the pressure accumulator to the proximal portion of the fluid pathway and configured to selectively relieve pressure in the proximal portion of the fluid pathway, wherein the apparatus has a first state in which the valve is closed and the pressure accumulator is not coupled to the fluid pathway to enable the first pressure source to maintain the collection device and the fluid pathway at a first sub-atmospheric pressure while the second pressure source charges the pressure accumulator to a second sub-atmospheric pressure more negative than the first sub-atmospheric pressure, and a second state in which the valve is opened and the second sub-atmospheric pressure from the pressure accumulator is introduced into the collection device and the fluid pathway.

9. The apparatus of claim 8, wherein the second pressure source comprises means for generating the sub-atmospheric pressure and providing the sub-atmospheric pressure to the pressure accumulator.

10. The apparatus of claim 9, wherein the means for generating the sub-atmospheric pressure comprises a pump.

11. The apparatus of claim 9, wherein the means for generating the sub-atmospheric pressure comprises an external suction source.

12. The apparatus of claim 8, wherein the pressure accumulator is configured to selectively provide sub-atmospheric pressure to the distal portion of the fluid pathway via the collection device.

13. A pleural drainage system comprising:
- a drainage catheter defining a drainage lumen and at least one drainage opening through which fluid is drawn into the drainage lumen from a pleural cavity;
- a fluid collector coupled to receive fluid from the drainage lumen of the drainage catheter, the fluid collector configured to receive a first sub-atmospheric pressure from a pressure source and communicate the first sub-atmospheric pressure to the drainage pleural cavity via the drainage lumen of the drainage catheter; and
- a suction system coupled to the fluid collector at a location outside of a fluid pathway extending between the drainage lumen of the drainage catheter and the fluid collector and configured to apply a first sub-atmospheric pressure to the drainage lumen in order to draw fluid into the drainage lumen through the at least one drainage opening, the suction system including a pump configured to selectively generate a second sub-atmospheric pressure, an accumulator in fluid communication with the pump and configured to store the second sub-atmospheric pressure generated by the pump, and a valve coupled between the accumulator and the fluid collector and configured to selectively couple the accumulator to the drainage catheter via the fluid collector;
- wherein the system has a first state in which the valve is closed and the accumulator is not coupled to the drainage catheter, and a second state in which the valve is opened and the sub-atmospheric pressure from the accumulator is introduced into the drainage catheter, the second state occurring when there is a blockage between the pleural cavity and the fluid collector, and the opening of the valve causing the sub-atmospheric pressure in the accumulator to be applied to the drainage catheter such that the blockage is drawn into the fluid collector.

* * * * *